(12) United States Patent
Bulman-Fleming et al.

(10) Patent No.: US 10,123,872 B2
(45) Date of Patent: *Nov. 13, 2018

(54) EXPANDABLE ANNULOPLASTY RING AND ASSOCIATED RING HOLDER

(71) Applicant: Coroneo, Inc., Montreal (CA)

(72) Inventors: Neil Bulman-Fleming, Courtenay (CA); Emmanuel Lansac, Malakoff (FR); Trong Tin Nguyen, Laval (CA); Anthony Paolitto, Ville Mont-Royal (CA); Jonathan Paquette, Blainville (CA); Adrian Ranga, Montreal (CA); Valerio Valentini, Montreal (CA)

(73) Assignee: Coroneo, Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/666,688

(22) Filed: Aug. 2, 2017

(65) Prior Publication Data

US 2017/0325957 A1    Nov. 16, 2017

Related U.S. Application Data

(63) Continuation of application No. 13/592,820, filed on Aug. 23, 2012, now Pat. No. 9,757,231, which is a (Continued)

(51) Int. Cl.
*A61F 2/24* (2006.01)
*A61B 17/04* (2006.01)

(52) U.S. Cl.
CPC ........ *A61F 2/2445* (2013.01); *A61B 17/0469* (2013.01); *A61F 2/2427* (2013.01); *A61F 2/2448* (2013.01); *A61F 2/2466* (2013.01); *A61F 2/2496* (2013.01); *A61F 2220/0008* (2013.01); *A61F 2220/0075* (2013.01); *A61F 2230/0013* (2013.01); *A61F 2230/0017* (2013.01)

(58) Field of Classification Search
CPC ......... A61F 2/24; A61F 2/2427; A61F 2/2445
USPC ................................. 623/2.11–2.38
See application file for complete search history.

(56) References Cited

U.S. PATENT DOCUMENTS

| | | |
|---|---|---|
| 4,585,453 A | 4/1986 | Martin et al. |
| 4,602,911 A | 7/1986 | Ahmadi et al. |

(Continued)

FOREIGN PATENT DOCUMENTS

FR        2858543 A1    2/2005

*Primary Examiner* — Suzette J Gherbi
(74) *Attorney, Agent, or Firm* — Wood Herron & Evans LLP

(57) ABSTRACT

Devices and methods are provided for surgical repair of dilated aortic root to restore aortic valve competence while preserving native leaflets. In one aspect of the invention an expandable annuloplasty ring is provided for external placement at the base of a dilated aortic root. The expandable ring is capable of elastically expanding between a first diastolic diameter and a larger second systolic diameter to provide a physiologically representative surgical repair of the aortic root. In a further aspect of the invention, is provided a holder assembly for aortic annuloplasty ring and suitable for other cardiac valve prosthesis. The holder assembly consists of a holder body pivotingly coupled to a handle member through a ball-and-socket arrangement.

25 Claims, 30 Drawing Sheets

Related U.S. Application Data continuation of application No. 11/450,516, filed on Jun. 9, 2006, now Pat. No. 8,267,993.

(60) Provisional application No. 60/688,688, filed on Jun. 9, 2005.

(56) References Cited

U.S. PATENT DOCUMENTS

| | | |
|---|---|---|
| 4,655,218 A | 4/1987 | Kulik et al. |
| 4,679,556 A | 7/1987 | Lubock et al. |
| 4,683,883 A | 8/1987 | Martin |
| 4,801,015 A | 1/1989 | Lubock et al. |
| 4,865,600 A | 9/1989 | Carpentier et al. |
| 5,041,130 A | 8/1991 | Cosgrove et al. |
| 5,258,021 A | 11/1993 | Duran |
| 5,290,300 A | 3/1994 | Cosgrove et al. |
| 5,350,420 A | 9/1994 | Cosgrove et al. |
| 5,376,112 A | 12/1994 | Duran |
| 5,476,510 A | 12/1995 | Eberhardt et al. |
| 5,496,336 A | 3/1996 | Cosgrove et al. |
| 5,522,884 A | 6/1996 | Wright |
| 5,571,215 A | 11/1996 | Sterman et al. |
| 5,607,471 A | 3/1997 | Seguin et al. |
| 5,669,919 A | 9/1997 | Sanders et al. |
| 5,674,280 A | 10/1997 | Davidson et al. |
| 5,683,402 A | 11/1997 | Cosgrove et al. |
| 5,741,274 A | 4/1998 | Lenker et al. |
| 5,741,283 A | 4/1998 | Fahy |
| 5,843,177 A | 12/1998 | Vanney et al. |
| 5,843,178 A * | 12/1998 | Vanney ............... A61F 2/2445  623/2.36 |
| 5,972,030 A | 10/1999 | Garrison et al. |
| 5,984,959 A | 11/1999 | Robertson et al. |
| 6,019,790 A | 2/2000 | Holmberg et al. |
| 6,090,138 A | 7/2000 | Chasak et al. |
| 6,193,652 B1 | 2/2001 | Berky et al. |
| 6,231,602 B1 | 5/2001 | Carpentier et al. |
| 6,248,116 B1 | 6/2001 | Chevillon et al. |
| 6,264,691 B1 | 7/2001 | Gabbay |
| 6,283,993 B1 | 9/2001 | Cosgrove et al. |
| 6,319,280 B1 | 11/2001 | Schoon |
| 6,348,068 B1 * | 2/2002 | Campbell ............. A61F 2/2418  623/1.15 |
| 6,406,492 B1 | 6/2002 | Lytle |
| 6,558,416 B2 | 5/2003 | Cosgrove et al. |
| 6,689,163 B2 | 2/2004 | Lytle |
| 6,802,860 B2 | 10/2004 | Cosgrove et al. |
| 7,056,287 B2 | 6/2006 | Taylor et al. |
| 8,034,102 B2 | 10/2011 | Bulman-Fleming et al. |
| 8,114,155 B2 * | 2/2012 | McCarthy ............ A61F 2/2448  623/2.36 |
| 8,267,993 B2 * | 9/2012 | Nguyen ................ A61F 2/2445  623/2.11 |
| 9,326,858 B2 * | 5/2016 | Migliazza ............ A61F 2/2448 |
| 9,427,316 B2 * | 8/2016 | Schweich, Jr. ......... A61F 2/243 |
| 9,757,231 B2 * | 9/2017 | Bulman-Fleming ........ A61F 2/2445 |
| 2002/0095070 A1 | 7/2002 | Furnish et al. |
| 2004/0034380 A1 | 2/2004 | Woolfson et al. |
| 2004/0054406 A1 | 3/2004 | Dubson et al. |
| 2005/0065597 A1 | 3/2005 | Lansac |
| 2005/0165478 A1 * | 7/2005 | Song ..................... A61F 2/2445  623/2.22 |
| 2007/0027536 A1 | 2/2007 | Mihaljevic et al. |
| 2008/0208331 A1 * | 8/2008 | McCarthy ............ A61F 2/2448  623/2.37 |
| 2011/0184511 A1 * | 7/2011 | Brunnett ............... A61F 2/2445  623/2.36 |
| 2011/0190878 A1 * | 8/2011 | Shu ..................... A61F 2/2409  623/2.4 |
| 2012/0143322 A1 * | 6/2012 | McCarthy ............ A61F 2/2445  623/2.36 |
| 2014/0257476 A1 * | 9/2014 | Montorfano ......... A61F 2/2409  623/2.38 |

\* cited by examiner

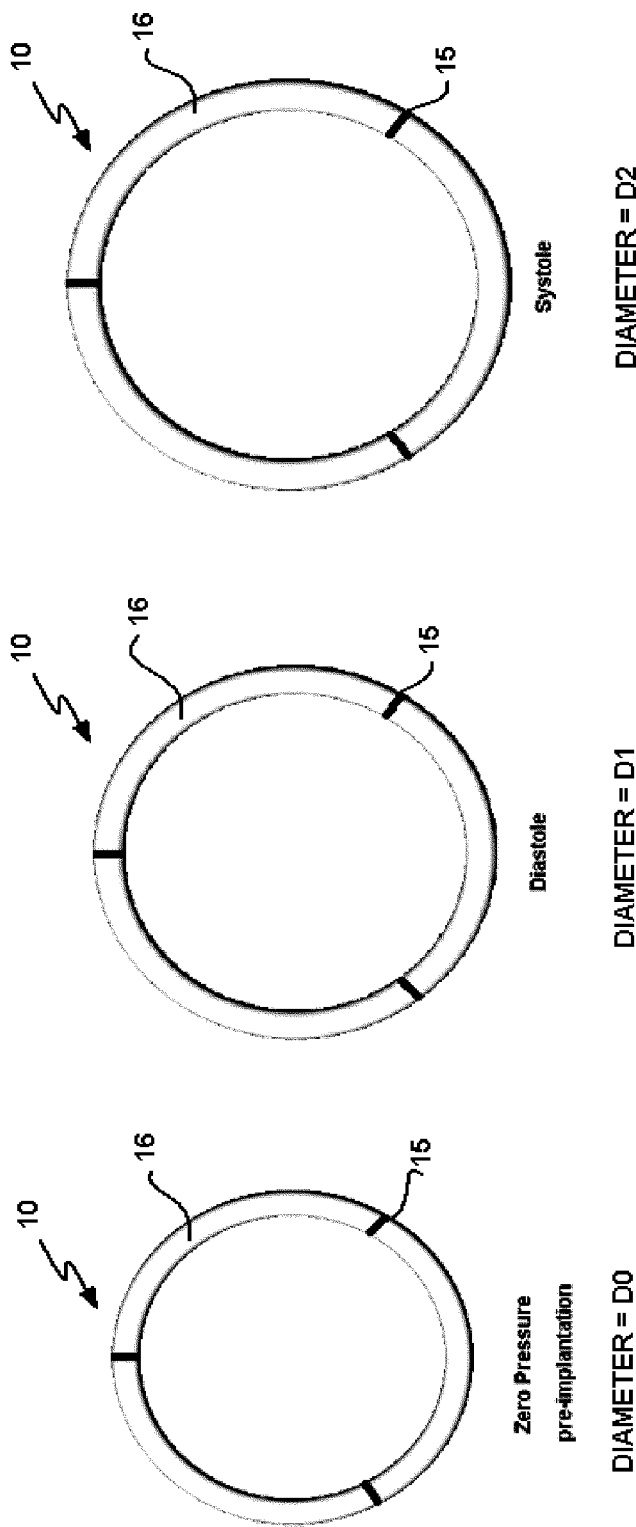

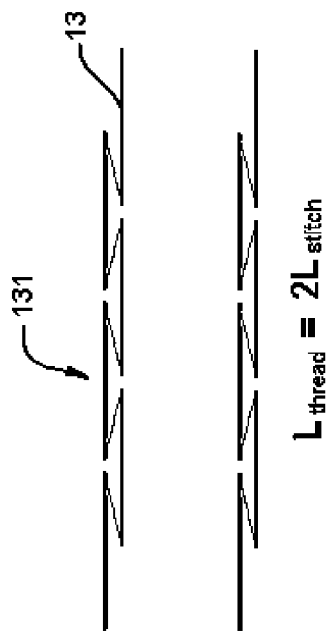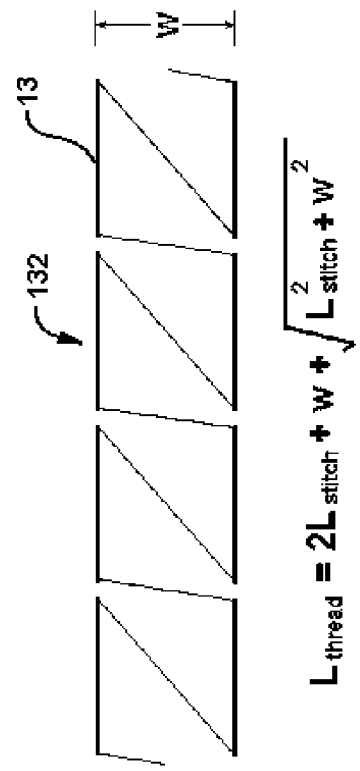
FIGURE 4A
FIGURE 4B

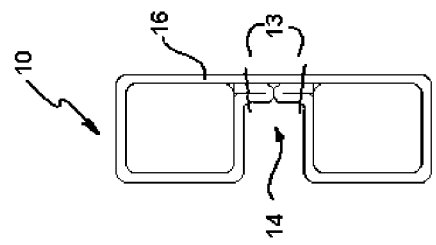
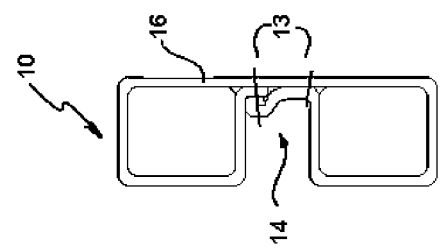
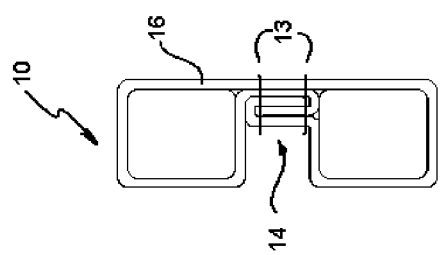
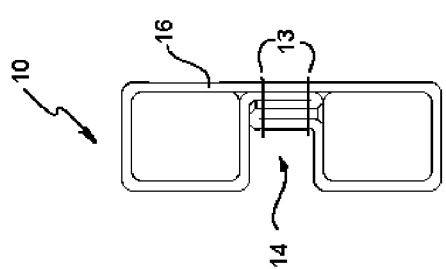
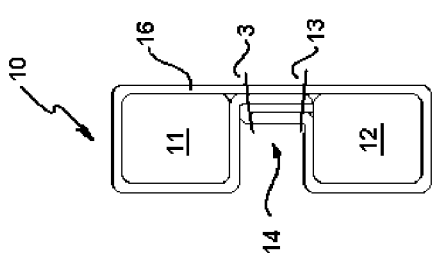

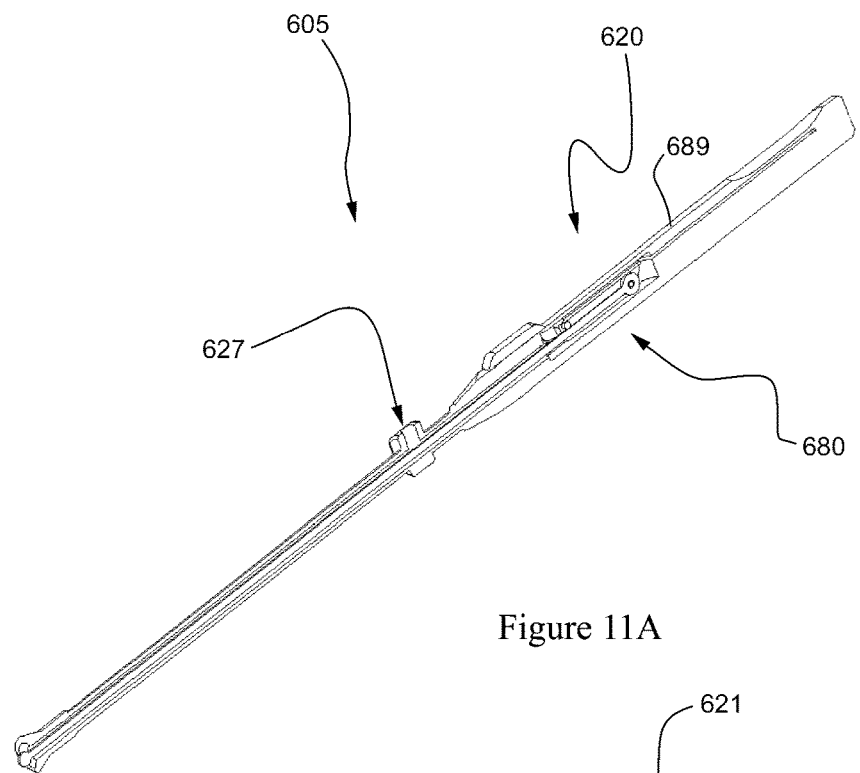
Figure 11A
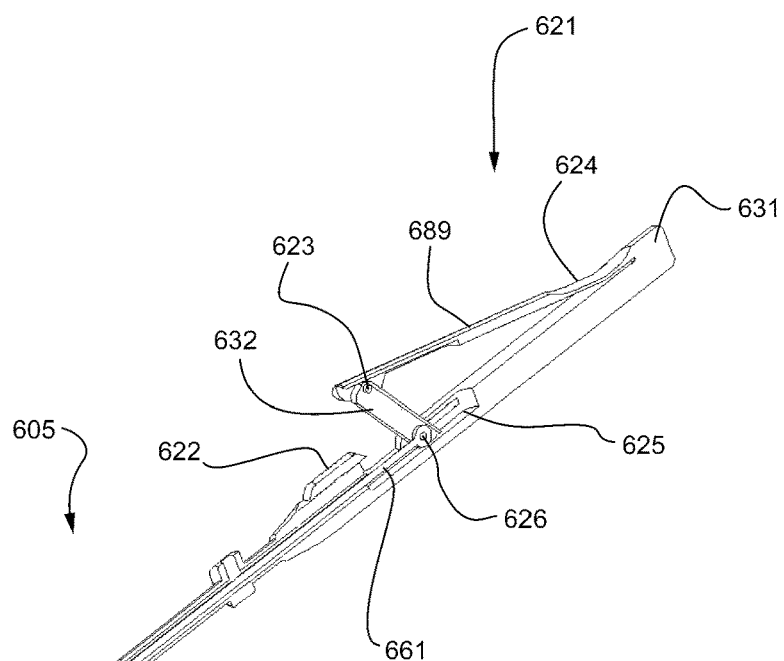
Figure 11B

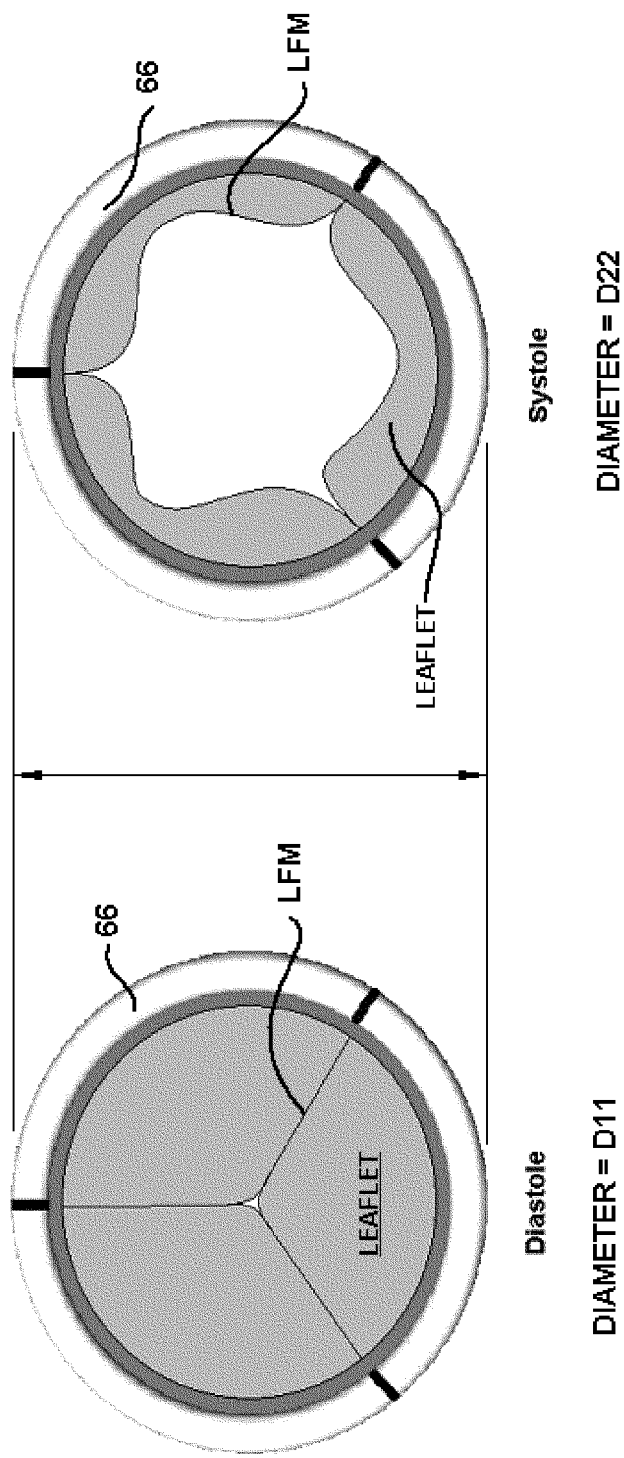

EXPANDABLE ANNULOPLASTY RING AND ASSOCIATED RING HOLDER

CROSS-REFERENCE TO RELATED APPLICATIONS

This application is a continuation of U.S. patent application Ser. No. 13/592,820, filed Aug. 23, 2012 (pending) which is a continuation of U.S. patent application Ser. No. 11/450,516, filed Jun. 9, 2006 (now U.S. Pat. No. 8,267,993) which claims the benefits of U.S. Provisional Patent Application Ser. No. 60/688,688 filed on Jun. 9, 2005, the disclosures of which are hereby incorporated in their entirety.

FIELD OF THE INVENTION

The present invention relates to the field of heart valve surgery and associated apparatus for holding cardiac valve prostheses during such surgical interventions. More specifically, the present invention is concerned with an implantable annuloplasty ring for aortic valve repair and its associated ring holder assembly.

BACKGROUND OF THE INVENTION

Annuloplasty rings to repair cardiac valves have been used mostly for mitral and tricuspid valve repairs. Such rings are implanted within the heart chambers and are as such in direct contact with patient's blood flow.

Many designs of annuloplasty rings have evolved over the years. Some rings are completely closed while others are partially closed. Two schools of thought still persist: one school advocates a rigid ring is best to resize the mitral or tricuspid valve annulus, while a second school believes it is best to resize the annulus with a non-rigid or flexible ring. The latter rings, although being non-rigid or flexible, are however generally not elastic and are as such not expandable as a function of the varying cardiac cycle parameters and associated ventricular mechanics. The latter rings passively comply to the desired shape in which the surgeon implants them during the surgical repair procedure, or if they are flexible may flex passively during the varying phases of the cardiac cycle.

Annuloplasty rings for the aortic valve are currently not commercially available and generally not used. Some aortic annuloplasty ring concepts placed internally to the aortic root, in the vicinity of aortic leaflets, have been tried with little or no success in correcting aortic insufficiency. This may be due to a number of reasons including the relatively more complex anatomy of the aortic valve annulus which is coronet shaped (unlike the mitral and tricuspid annuli which are generally planar), and the dynamics of the aortic root which expands considerably between the diastolic and systolic phase in the cardiac cycle.

Consequently, current aortic valve surgery is mostly dominated by valve replacement procedures. More specifically, in treating aortic valve insufficiencies due to an increasingly widespread range of pathological conditions (including Marfan disease, aortic annulo-ectasia, idiopathic root dilations, bicuspid valve disease with associated aneurysm, and acute aortic dissection), very few aortic valve repair procedures are practised to restore competence to the native aortic valve while preserving native leaflets. This is largely due to the technically demanding nature of current valve repair or sparing procedures such as the most common "David Reimplantation" or "Yacoub Remodelling". Moreover, due to the lack of a standardized technique that would advantageously rely on enabling apparatus and cardiac prosthesis specifically designed to facilitate the aortic valve sparing procedure with a physiologically representative reconstruction, current surgical interventions are sometimes characterized by surgeon-dependent outcomes. Due to this lack of specially designed prosthesis and apparatus, practicing surgeons must often resort to "off-label use" of existing implant materials to tailor a surgical solution during the surgical intervention.

Due to the above drawbacks, even though a patient suffering from a dilated aortic root may have viable valve leaflets, currently in the great majority of cases, the native valve and aortic root are removed and are replaced by a valved synthetic conduit in a procedure known as the "Bentall" procedure. As a result, the patient's leaflets are not preserved but are instead replaced by a prosthetic mechanical valve, and the patient's dilated aortic root is not resized but removed and replaced by synthetic conduit such as Dacron or ePTFE. One of the main drawbacks of the Bentall procedure is that the patient is placed on long-term anticoagulation therapy in Bentall procedures using mechanical valves, and a risk of valve degradation and need for re-operation in Bentall procedures using a bioprosthetic valve.

In recent years, the scientific literature reflects a significant effort in the medical research community directed not only to an understanding of the functional anatomy or physiology of the aortic valve and root complex, but to the development of surgical repair techniques that are able to preserve viable native leaflets while correcting aortic insufficiency. Such surgical repair techniques are commonly referred to as "valve-sparing surgeries".

The valve sparing surgery commonly known as "David Reimplantation" involves the placement of a Dacron root prosthesis or synthetic aortic conduit over the scalloped native tissue, where it is sutured both below the valve leaflets through the valve annulus, and above the valve leaflets. The procedure is generally long and difficult to perform, and often results in leaflet impact or concussion with the walls of the Dacron prosthesis during the ejection phase of the cardiac cycle. In addition, the absence of radial compliance of the Dacron root prosthesis does not allow for an increase in diameter at the sinotubular junction STJ during ejection, which is an important aspect in providing optimal blood transport while preserving valve dynamics and valve leaflet durability. As such, the normal valve physiology is compromised in this valve-sparing intervention.

The second type of valve sparing operation, commonly known as "Yacoub Remodelling", involves scalloping the Dacron root prosthesis to essentially match the remaining native tissue, and using a running suture to attach the prosthesis to the native aortic root tissue. Although this method addresses some of the problems of the reimplantation method, it does not directly constrain the valve annulus diameter, which has been seen to result in annular dilatation over time. As such, this procedure is not well suited for resizing a dilated valve annulus, and may be limited to replacing aneurysmal aortic tissue. Since it also relies on a Dacron vascular conduit, which is radially non-expansible, the expansion of the aortic root at level of commissures, in the plane joining the commissures or scalloped peaks of native tissue, tends to be constrained by the conduit fabric hoop. As such, the leaflet free edges are hindered in assuming their triangulated relationship, since the plane containing the sinotubular junction (STJ) is generally not expansible in this surgical procedure. Unlike the reimplantation procedure, however, the leaflets have a lower likelihood of hitting the conduit wall since pseudo-sinuses may be fashioned from a scalloped Dacron conduit to recreate the pouch-like configuration seen in a healthy aortic root. Nonetheless, in the remodelling valve-sparing intervention, the normal native valve physiology is compromised, and the effectiveness of resizing a dilated aortic annulus, or preventing its future dilatation, with a scalloped vascular conduit remains questionable.

Although useful and widely accepted for some aortic reconstruction procedures, conventional valve-sparing procedures and devices nevertheless suffer from numerous drawbacks or shortcomings that are manifested and become apparent both during the operative and post-operative periods.

Accordingly, there exists a need for an improved aortic root reconstruction procedure, and enabling devices, that allows correction of a dilated aortic annulus (with associated replacement of aneurysmal aortic tissue when applicable), while preserving the native leaflets and maintaining normal valve physiology. Typical prior art devices and methods for aortic reconstruction or valve sparing interventions do not offer a dynamic device configuration that may advantageously vary during the different phases of the cardiac cycle, and consequently restore or preserve normal aortic valve physiology. More specifically, there exists a need for such an expandable annuloplasty ring which, when implanted, dynamically controls the valve annulus at the level of the aortic root where it is implanted. Such an expandable annuloplasty ring would provide the many benefits including: resizing of a dilated aortic root or annulus in a physiologically representative manner, restoring native leaflet coaption and valve competence during diastolic phase of cardiac cycle, improved blood flow through the open aortic valve during the systolic phase of the cardiac cycle, minimized stresses on native leaflets as they are cycled from their diastolic to systolic configuration. Also beneficial would be a procedure with reduced time and difficulty relative to current valve sparing procedures.

Cardiac valve prostheses are generally mounted on a holder assembly to facilitate their manipulation during the course of a surgical intervention and their implantation. Current holder assemblies are characterized by a number of drawbacks.

A great majority of holders are configured with a rigid handle and a fixed orientation of the holder body or prosthesis carrier relative to the handle. Such a mechanical limitation does not allow the surgeon to orient the holder body relative to the handle in order to optimize the delivery of the prosthesis to the implant site. Some holder assemblies have been configured with malleable handles in an attempt to alleviate this drawback. However, such malleable handles are generally difficult to reshape in different bent configurations once they have been initially bent. Moreover, the material of such malleable handles work hardens with repeat bending making it progressively more difficult to easily bend such handles. As a result, some holder assemblies have introduced shape memory alloys, such as Nitinol, for the material of the handle. Handles made from Nitinol that would be bent during the surgical procedure would resume their straight unbent shape after being exposed to sterilization temperatures. Some of the drawbacks associated with Nitinol handles include cost, and generally insufficient stiffness of such handles given the highly elastic properties of Nitinol. In order to make Nitinol handles malleable and easy to bend into the desired shape by the surgeon, such Nitinol handles are equally easy to bend out of desired shape when the cardiac prosthesis mounted on end of such handles is exposed to tissue or suture loads during the surgical intervention.

A great number of holder assemblies are configured with a threaded interface between the handle and the prosthesis carrier or holder. Such threaded interfaces do not provide the ability to orient the holder body relative to the handle. As well, such threaded interfaces generally do not provide ability for rapid changeover of prosthesis holders or sizers, since unthreading and rethreading is a relatively lengthy process with inherent risks of cross-threading. Current alternatives to threaded interfaces, such as quarter turn bayonet arrangements, are also currently used but also do not offer the ability to orient the holder body relative to the handle. Such bayonet arrangements are relatively large in size thereby creating greater obstruction to the surgeon view of the surgical site. Such obstruction is particularly problematic when the surgeon is visually assessing the suitability of a selected size of prosthesis. Also, bayonet arrangements are generally more difficult to clean and sterilize given the design of cooperating bayonet features such as blind holes and elongated slots and dogs.

Another current technique for coupling the handle to the holder or prosthesis carrier consists of a tapered distal tip on the handle which is pressed into a similar cooperating tapered opening in the holder. This provides a friction fit which may be separated by applying a separation force between the holder and the handle. This technique does not provide a positive lock between the handle and holder (or sizer) and the engagement forces may vary due to dimensional tolerances and wear at such interfaces. Moreover, it may be difficult to remove the holder from the handle when the holder is placed adjacent to the native valve during the surgical intervention, due to the variability in frictional engagement and since the separating force must be applied to the holder in the chest cavity while the handle is pulled away from the holder away from the chest cavity. Alternatively, the friction fit may be too loose resulting in holder (or sizer) easily disengaging from the handle making for an unsecure assembly. Other types of holder to handle interfaces rely on similar distal disengagement features whereby if the need to detach the handle from holder arises during the surgical procedure, the surgeon generally needs to get inside the chest cavity to separate the holder from the handle.

Due to the current lack of suitable mechanical interfaces to allow rapid changeover between different sizers and a common handle, and a secure engagement during the sizing intervention, current sizers are each integrally mounted to their own separate handle.

Accordingly, there exists a need for a holder assembly that resolves the drawbacks associated with current holders. More specifically, there is a need for a holder assembly that allows rapid quick changeovers. There is a need for holder assembly that allows the holder or prosthesis carrier to be variably mounted in a number of secure orientations relative to handle so that the optimum mounting arrangement can be selected to suit the specific anatomy of the patient, the specific anatomic routing of the surgical approach, or the surgeon work preference.

In accordance with the aortic annuloplasty ring of the present invention there exists the need for a specially designed holder assembly to mount an elastic or expansible annuloplasty ring in a mounting configuration that is similar to a physiologic configuration that it will be exposed to in-vivo, such as physiologic configuration being different to the free state configuration of the ring. Such a holder will allow the surgeon to assess the suitability of a ring size while the ring is held in an in-vivo configuration prior to removing the elastic ring from its holder, and allowing it to resume its free state configuration.

SUMMARY OF THE INVENTION

The invention provides devices and surgical methods for performing valve sparing surgery of the aortic valve.

In accordance with a first aspect of the present invention, there is provided an expandable annuloplasty ring for surgical repair of a cardiac valve, the annuloplasty ring comprising: a first elastic core member and a second elastic core member, the first and second elastic core members held in general register and in a spaced apart relationship to each other by a sheath member, the sheath member at least partially encapsulating a portion of each of said first and second core members, the annuloplasty ring being movable between a first diastolic configuration and a second systolic configuration wherein when the annuloplasty ring is in the diastolic configuration the annuloplasty ring allowing resizing of a dilated aortic root so as to provide adequate coaption of valve leaflets contained within resized dilated aortic root, and wherein when the annuloplasty ring is in the systolic configuration the annuloplasty ring is in an expanded perimeter relative to the diastolic configuration allowing the valve leaflets within the aortic root to open; the annuloplasty ring movable between the first and second configuration by virtue of pressure changes that occur within the aortic root and muscle contractions that occur in the heart tissue surrounding the annuloplasty ring as a function of the cardiac cycle.

The annuloplasty ring according to the present invention allows for surgical reconstruction of a dilated aortic root while preserving native valve leaflets or cusps in a manner that is physiologically representative. The implanted annuloplasty ring allows the native aortic root and cardiac valve contained therein to generally retain their dynamic behavior as a function of the variable pressures, muscle contractions, and blood flows associated with the dynamic cardiac cycle.

Furthermore, the annuloplasty ring according to the present invention is configured and sized to be implanted on the external surface of the aortic root, thus reducing the likelihood of thromboembolism and other like complications associated with internally-placed, blood-contacting annuloplasty rings.

Still furthermore, unlike internally placed annuloplasty rings which rely on placement sutures between the ring and annulus to carry the load associated with resizing the valve annulus, the annuloplasty ring placed on the external surface of the aortic root acts as an external brace or hoop member. As such, the placement sutures between the annuloplasty ring and aortic root serve mostly only to locate the ring axially, relative to the aortic root. The loads associated with resizing the dilated annulus are carried entirely by core members of the externally placed annuloplasty ring.

Still furthermore, the annuloplasty ring and associated ring holder according to the present invention are designed so as to facilitate current valve sparing surgeries by providing a standardized valve sparing procedure through a set of quick and ergonomic steps.

In another preferred embodiment according to the first aspect of the present invention is provided a split annuloplasty ring whose free ends are subsequently joined to so that split ring behave as a full and complete annuloplasty ring. Such a split annuloplasty ring allows it to be implanted at the base of the aortic root, below the level of the left and right coronary ostia, without the need to detach the coronary buttons. Such a split ring is particularly suited for valve sparing surgeries without associated aneurysm of the aortic tissue and without resection of the Sinus of Valsalva tissue.

In a further aspect of the invention, a holder assembly for the aortic annuloplasty ring is provided. The holder assembly facilitates mounting of the aortic annuloplasty ring external to the aortic root, and is advantageously provided with spaced apart suture access windows to facilitate placement of ring fixation sutures. The holder assembly is advantageously provided with a mechanical interface that pivotingly couples a holder body, configured and sized for holding the aortic annuloplasty ring, and a handle member. The holder body may be oriented relative to the handle member within a free range of orientations, and may be locked in a predetermined spatial position within this range of possible orientations. The invention also provides for an actuator coupled to said handle for locking said holder body in said predetermined spatial position. The invention also provides for the holder to be detachable from said handle to allow changeover of holders or prosthesis sizers from a common handle.

In further aspect of invention, the inventive features of the holder assembly may be advantageously applied to holder assemblies for other cardiac valve prostheses such as annuloplasty rings for mitral or tricuspid valve repairs, or to holder assemblies for cardiac valves (aortic, mitral, tricuspid valves either mechanical or bioprosthetic, and allograft or homograft if said latter graft valves are mounted to a holder body or carrier prior to surgical implantation). More specifically, a holder assembly for implanting a cardiac valve prosthesis is provided, said holder assembly comprising a holder body configured and sized for holding the cardiac valve prosthesis, and a handle member configured to be gripped during the implantation of the cardiac valve prosthesis. The handle member also being pivotingly coupled to the holder body through a ball-and-socket arrangement wherein the holder body is pivotable relative to said handle in a desired spatial orientation through said ball-and-socket arrangement.

In further aspect of invention, the inventive features of the holder assembly may be advantageously applied to cardiac valve sizers used for selecting the appropriate size of a cardiac valve prosthesis to be implanted.

A further understanding of the nature and advantages of the invention may be realized by reference to the remaining portions of the specification and the drawings.

BRIEF DESCRIPTION OF THE DRAWINGS

Various embodiments of the present invention will now be disclosed, by way of example, in reference to the following drawings in which:

FIGS. 2A-2C in top views of the annuloplasty ring of FIG. 1 illustrate the variable diameter of the annuloplasty ring when exposed to varying internal pressures ranging from zero pressure at pre-implantation in FIG. 2A, diastolic pressure (@80 mmHg) in FIG. 2B, to systolic pressure (@120 mmHg) in FIG. 2C;

FIG. 4A in a schematic view illustrates a first alternative for a stitch pattern to assemble components of the annuloplasty ring according to the present invention;

FIG. 4B in a schematic view illustrates a second alternative for a stitch pattern to assemble components of the annuloplasty ring according to the present invention;

FIGS. 4C-4G in schematic sectional views illustrate a variety of methods for configuring sheath and stitching patterns to assemble components of annuloplasty ring according to the present invention;

FIGS. 11A-11B illustrate a variant handle member 505 having a variant actuator 680 according to the present invention;

FIGS. 13A-13B in top views illustrate the effect of having a non-expandable annuloplasty ring on the leaflet bending as a function of the cardiac cycle from diastole in FIG. 13A to systole in FIG. 13B;

DETAILED DESCRIPTION

Figure 1:
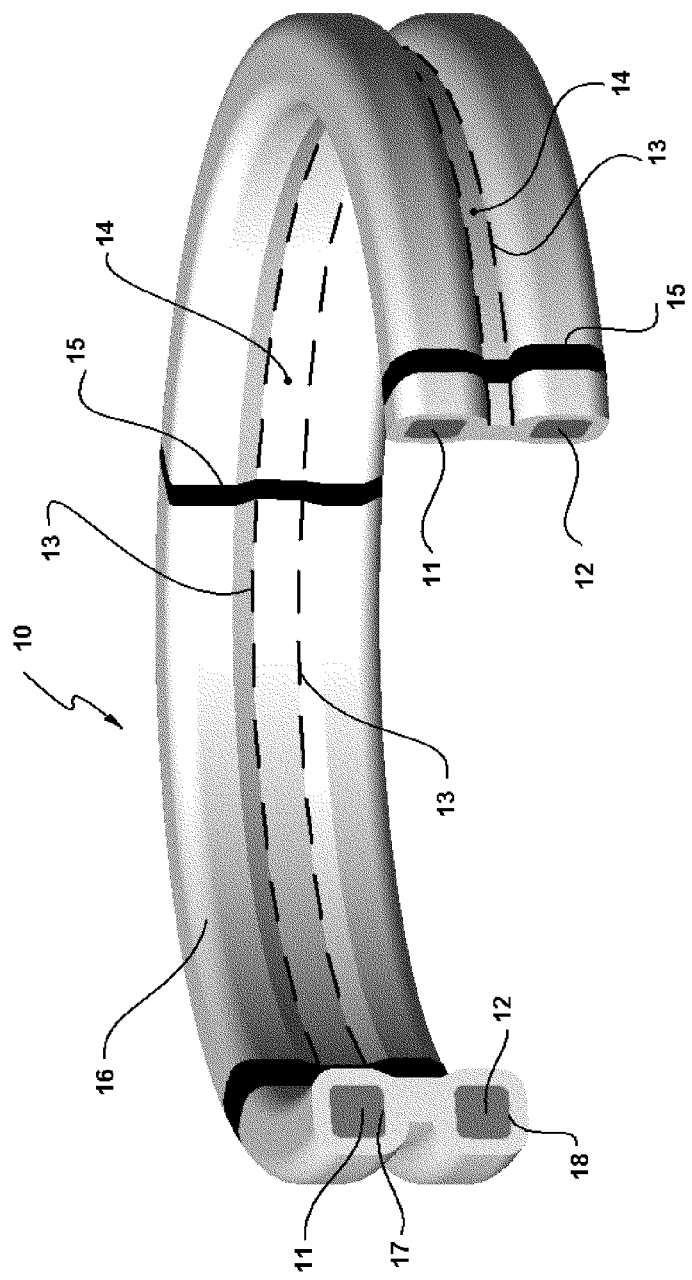
FIG. 1 in a perspective cutaway view illustrates an expandable annuloplasty ring in accordance with an embodiment of the present invention for use in aortic valve sparing surgery.

Referring to FIG. 1, there is shown an annuloplasty ring 10 in accordance with an embodiment of the present invention. The annuloplasty ring 10 is described herebelow and shown throughout the figures in the context of an aortic annuloplasty ring used to repair an aortic valve with aortic insufficiency. It should however be understood that the expandable annuloplasty ring 10 may offer advantages in other contexts, such as surgical repair of other cardiac valves like the pulmonary valve, without departing from the scope of the present invention.

In a preferred embodiment, annuloplasty ring 10 is comprised of a first core member 11 and a second core member 12. Each of said core members 11,12 have a substantially annular shape and are preferably made from an elastic material such as silicone elastomer, polyvinyl-alcohol based hydrogels or cryogels, polyurethanes, synthetic or natural rubbers, or any other like elastic materials suitable for implantation and capable of providing ring 10 with its expandable or expansible properties according to the principles of the present invention.

As illustrated in FIG. 1, each of core members 11,12 have a substantially square cross-sectional area with rounded corners that remains substantially constant around the perimeter of the core. Alternatively, core members 11 and 12 may be configured with different cross-sectional areas. Alternatively still, the cross-sectional area may be varied around the perimeter of said core members so as to provide increased flexibility or stiffness at different sections of the annuloplasty ring perimeter. Yet alternatively still, the core members 11,12 may be designed with a cross-sectional area that is circular, elliptical, triangular, rectangular, or any other like geometric shape without departing from the spirit of the present invention. Core members 11,12 may also be reinforced by fibres or filament members in a suitable fibre-reinforced arrangement to provide an annuloplasty ring with non-linear elastic behavior as a function of ring expansion.

The cross-sectional area of the core members 11,12 is derived and depends on the material properties of the elastic material selected for said core members. For a given selected material, having a characterizing modulus of elasticity, the cross-sectional area of the core members 11, 12 may be sized for example to provide enough stiffness to annuloplasty ring 10 to allow surgical resizing of a dilated aortic root thereby restoring leaflet coaption and valve competence when the aortic root is exposed to the diastolic phase of the cardiac cycle, and simultaneously to provide enough flexibility to allow controlled stretching of annuloplasty ring 10 as aortic root expands when exposed to the systolic phase of the cardiac cycle. The modulus of elasticity is preferably in a range that will yield a ring cross-sectional sufficiently compact to allow insertion of the annuloplasty ring below the coronary ostia, while also providing a ring with sufficient height that the resulting contact surface between ring 10 and the aorta is sufficient to adequately buttress the dilated native annulus in its resized diameter.

A preferred range of expansion of the annuloplasty ring 10 between the diastolic and systolic phase of the cardiac cycle is between 5 and 20%, and preferably between 8 and 15% and most preferably between 10 and 12%, thereby approximating the dynamic aortic root in a healthy patient. FIGS. 2A-2C and 3A-3C illustrate an example of the preferred embodiment of annuloplasty ring 10 for implantation at the base of the aortic root, having a systolic diameter D2 greater than the diastolic diameter D1 by 10%, and the diastolic diameter D1 greater than the per-implantation diameter D0 by 10%. It is understood that the same annuloplasty ring may expand by different amounts depending where on the aortic root it is implanted. For instance, a ring implanted at the level of the sinotubular junction (STJ) will be exposed to different boundary conditions than a ring implanted at the base of the aortic root. Consequently, the same ring will expand different amounts between diastole and systole depending on where it is implanted, that is, at the STJ or at the base of the aortic root. As such, rings may be designed for particular implantation locations by taking into account the different boundary conditions they will be exposed to. Generally, the STJ ring is exposed to smaller variations in cardiac cycle pressures than a ring at the base of the aortic root, which is influenced to a greater degree by the muscular contractions of the left ventricular outflow tract (LVOT).

Figure 3C:
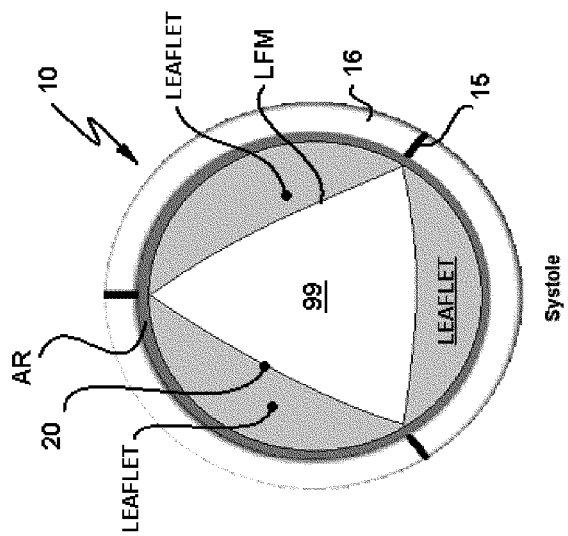
FIGS. 3A-3C in top views of the annuloplasty ring of FIG. 1 illustrate the relationship of the variable diameter of the annuloplasty ring to the aortic root and valve leaflets.
Figure 3B:
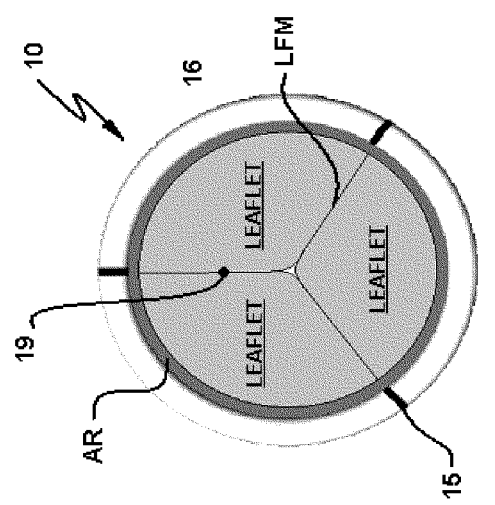
Figure 3A:
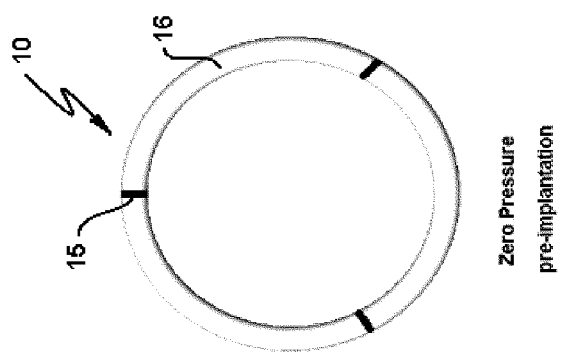
Figure 8A:
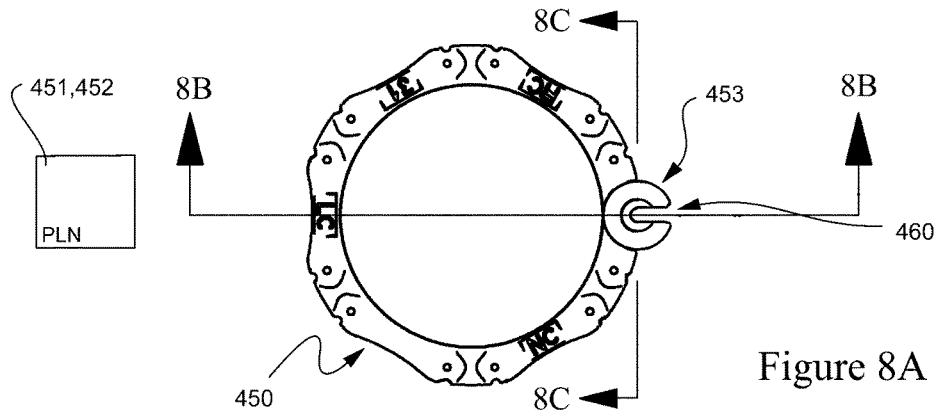
FIGS. 8A-8H illustrate a holder assembly for annuloplasty ring 10 as well as the range of orientations provided by ball-and-socket mechanical joint 406.
Figure 8B:
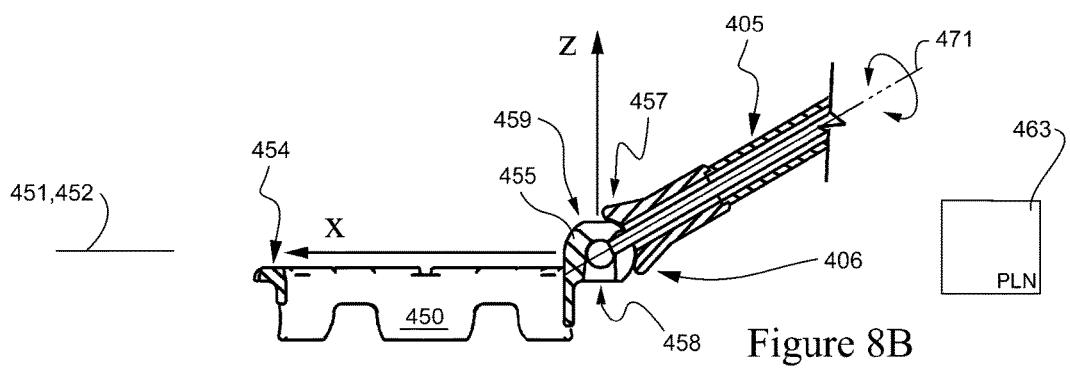

Referring to FIGS. 3B-3C, one of the benefits of having an expandable annuloplasty ring 10, relating to native leaflet stresses is illustrated. The proposed expandable annuloplasty ring 10, allowing the aortic root AR to expand in a controlled manner from its diastolic diameter (FIG. 3B) to its systolic diameter (FIG. 3C), advantageously allows leaflet stresses to be reduced or minimized as leaflet free margin LFM straightens from its obtuse-angle, L-shape configuration 19 during the diastolic phase of the cardiac cycle, to a substantially straight configuration 20 during the systolic phase of the cardiac cycle. As such, the expansion of the aortic root AR as controlled or modulated by the expanding annuloplasty ring 10 attached thereto, tends to minimize the amount of cyclic bending that the leaflet free margin LFM is repeatedly exposed to during the cardiac cycle, thereby also reducing the bending stresses and improving long-term durability of the native leaflets. Consequently, the native leaflets behavior is substantially preserved by the surgical repair technique associated with an expandable annuloplasty ring 10, and consequently a resizing of the dilated aortic root may be achieved in physiologically representative manner. In contrast, the effect of a non-expandable annuloplasty ring 66 on leaflet stresses is illustrated in FIG. 8B. The non-expandable annuloplasty ring 66, constraining the aortic root AR from expanding (from its diastolic to systolic diameter), augments leaflet stresses as leaflet free margin LFM inflects its configuration from an obtuse-angle, L-shape configuration during the diastolic phase (FIG. 8A), to a substantially double-S-shaped configuration during the systolic phase (FIG. 8B) of the cardiac cycle. The constrained aortic root AR restricted by a non-expanding annuloplasty ring 66 attached thereto, increases the amount of cyclic bending that the leaflet free margin LFM is repeatedly exposed to during the cardiac cycle, thereby also increasing the bending stresses and compromising the long-term durability of the native leaflets. In addition, there exists a greater risk of leaflet concussion and erosion with a non-expandable annuloplasty ring 66 since the leaflet free margins LFM may contact the aortic root wall AR (or wall of synthetic conduit) during the systolic phase of the cardiac cycle.

Another benefit provided by expandable annuloplasty ring 10 relates to the improved flow through area 99 across the aortic valve during the systolic phase of the cardiac cycle. This improved flow through area 99 is illustrated in FIG. 3C as the leaflet free margins LFM form a substantially triangular opening. In contrast, the effect of a non-expandable annuloplasty ring 66 on flow through area 199 is illustrated in FIG. 8B. The systolic diameter D22 being substantially equal to the diastolic diameter D11 does not provide the increased flow through area that an expandable annuloplasty ring 10 provides as leaflet free margins LFM try to move radially outward within a constrained aortic root.

In the preferred embodiment of annuloplasty ring 10, each of the core members 11,12 is covered by textile material or fabric sheath 16. Sheath 16 is preferably sewn in a manner to enclose each of said core members 11,12 in a separate textile channel 17,18, respectively. As such, sheath 16 acts as a casing for core members 11,12, thereby serving to maintain the spatial relationship between said core members. As illustrated, sheath 16 keeps core members 11,12 generally parallel and spaced apart relative to each other. Alternatively, sheath 16 can be configured to keep core members in a non-parallel spaced apart relationship. Alternatively still, sheath 16 can be configured with a slight undulation at one or more circumferential locations to allow better seating of the annuloplasty ring at the base of the aortic root.

Sheath 16 is preferably designed not to hinder the core member expansion during cardiac cycle and as such contributes very little or not at all to the overall stiffness or flexibility of ring 10. Sheath 16 may be designed to set the maximum limiting ring diameter that the annuloplasty ring 10 will be able to assume, and as such provide a temporary failsafe feature in the event of a core failure.

Choice of sheath 16 materials include polyester, Dacron™ Goretex™ or other like textile materials that are knit (preferably) or woven in a manner that does not inhibit the expansion of core members 11,12 during the cardiac cycle (i.e. the physiologic range). Alternatively, sheath 16 can also be made of expandable ePTFE, or elastomeric membrane exhibiting much greater flexibility than the elastic material selected for the core members 11,12. Alternatively, sheath 16 may be designed with limited expansibility so as to contribute to the overall stiffness and flexibility of annuloplasty ring 10. Alternatively still, sheath 16 may be configured with varying expansibility as a function of the perimeter location, as for example with greater flexibility at the level of the nadirs and less flexibility proximal to the interleaflet triangles.

The portion of sheath 16 that maintains core members 11,12 in a spaced apart relationship advantageously provides a substantially annular suturing zone 14. In the preferred embodiment of ring 10, as illustrated in FIG. 1, suturing area is a continuous substantially cylindrical surface. Alternatively, suturing zone 14 may also be discontinuous having for example a plurality of fenestrations or openings extending therewithin. Suturing zone 14 may be advantageously delimited by two circumferential stitch lines 13 so as to provide surgeon with visual markers clearly delineating the zone within which to place a plurality of ring anchoring sutures, preferably U-stitches to anchor the ring to the aortic root as described below. As such, the present invention provides an annuloplasty ring 10 having clearly identified suturing zone 14 located between each of the elastic core members 11,12. Said suturing zone 14 is preferably clearly delineated by stitch lines 13 that are visible both on the internal and external surfaces of ring 10. Any suitable visible array of markers may be incorporated in ring 10 so as to assist the surgeon in adequately spacing an array of ring retention sutures during the surgical intervention.

FIGS. 4A and 4B illustrate a first and second alternative for a stitch pattern 131, 132 that creates a stitch line 13 capable of providing a clearly delineated suture zone 14. In FIGS. 4A and 4B, bold lines represent the portion of stitch line 13 that is visible on the inside surface of ring 10, while the light lines are visible on the outside surface of ring 10. In the preferred embodiment of ring 10, stitch line 13 provides the closing seam to retain the elastic core members 11,12 within their respective textile channels 17,18 while being sufficiently compliant to not hinder or restrict the desired expansion of elastic core members 11,12 during the phases of the cardiac cycle. The compliance of the stitch line 13 is also required to avoid transferring the load from the expanding elastic core members 11,12 to sheath 16. Stitch lines 13 are preferably advantageously designed to not see any of the loads during annuloplasty ring functioning, and as such are less likely to contribute to a device failure.

FIGS. 4C-4G illustrate a variety of suitable methods for enclosing elastic core members 11,12 within sheath 16 in order to create a composite ring structure 10. In each of the above variants, two stitch lines 13 serve to form an expandable seam according to the principles of the present invention.

An annuloplasty ring 10 having two distinct core members 11,12 separated by a suturing zone 14 provides the following advantages (relative to a single core annuloplasty ring covered by a textile sewing cuff):

Since ring anchoring sutures are placed between the two distinct ring cores 11,12, substantially symmetrical loading of the elastic core members 11,12 relative to the ring anchoring sutures occurs during expansion of the aortic root, thereby preventing any "rolling" of the elastic core members over the ring anchoring sutures. Such an arrangement enhances ring stability and propensity of ring to roll up along the aortic root over the anchoring sutures as the aortic root pulsates.

The likelihood of piercing, nicking, or otherwise damaging an elastic core member 11,12 by placing ring anchoring sutures through the annuloplasty ring 10 is greatly reduced or eliminated by having a clearly delimited suturing zone 14 located between said core members. This allows a more precise prediction of durability and service life since puncturing an elastic core member 11,12 with a securing suture during ring implantation tends to affect the durability of the ring.

A clearly delimited suturing zone 14 leads to higher degree of repeatability between procedures performed by one surgeon and consistent standardized surgical method between surgeons.

A clearly delimited zone between core members 11, 12 results in ease of suturability of the annuloplasty ring since anchoring sutures may easily be passed through textile sheath in said delimited zone by avoiding core members 11, 12.

Figure 6:
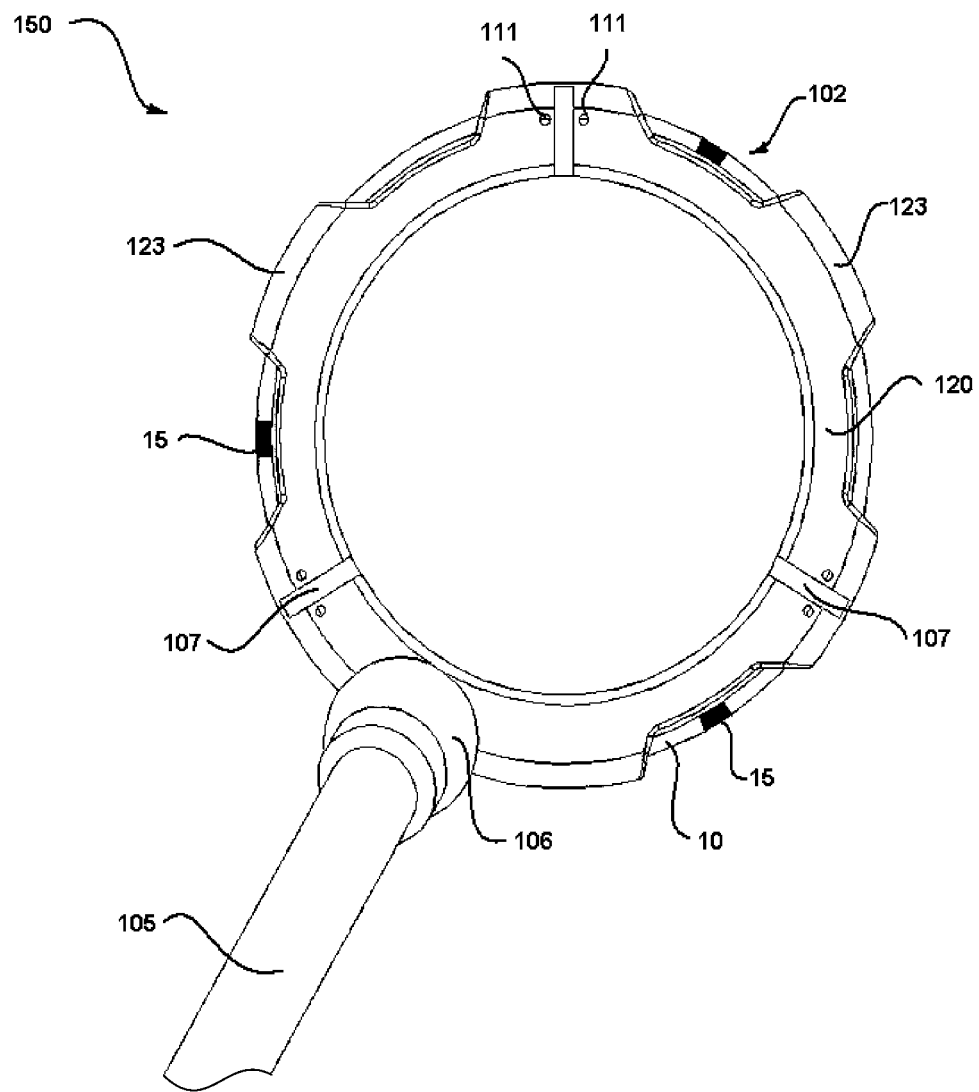
FIG. 6 is a top view of the annuloplasty ring holder illustrated in FIG. 5 illustrating in greater detail the feature of the detachable ring holder portion.

To facilitate annuloplasty ring positioning during surgical implantation, ring 10 may be advantageously provided with a plurality of positioning indicators 15. As illustrated in FIGS. 1 and 6, three such positioning indicators 15 are provided as demarcations within sheath 16 located 120 degrees apart from each other. Alternatively, ring 10 may be provided with six equally spaced positioning indicators, or any advantageous number that will assist surgeon in strategic positioning of ring 10 relative to anatomic landmark within the aortic root, such as a commissure. Such features may be timed with features on the ring holder to facilitate the implantation procedure.

Figure 14B:
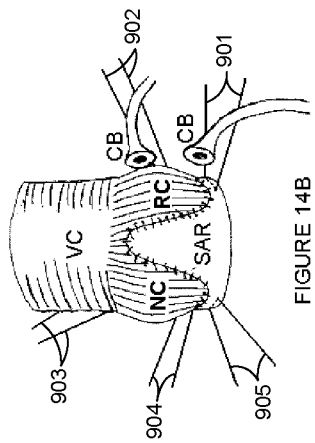
FIGS. 14A-14D in schematic elevational views illustrate the implantation steps of the aortic annuloplasty ring of FIG. 1 in a leaflet valve sparing surgery whereby a portion of aortic root has been removed and replaced by a synthetic conduit.
Figure 14D:
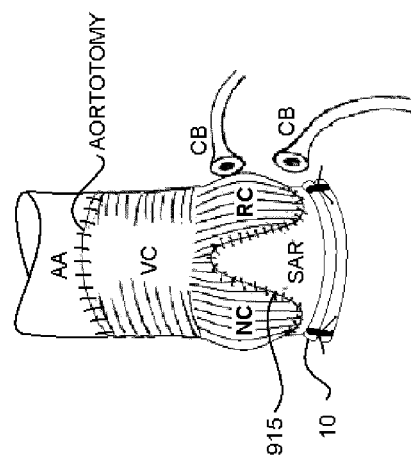
Figure 14A:
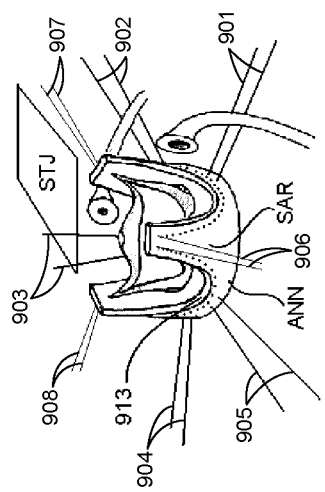
Figure 14C:
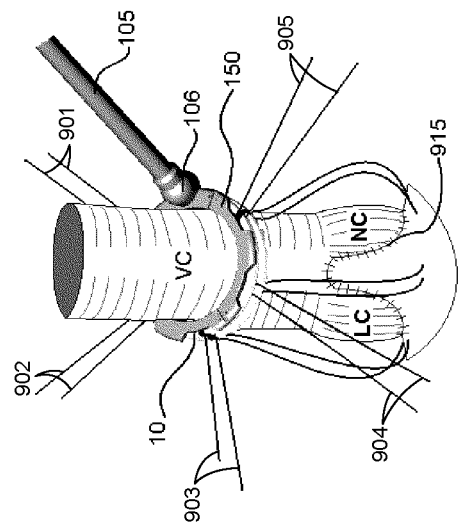
Figure 16A:
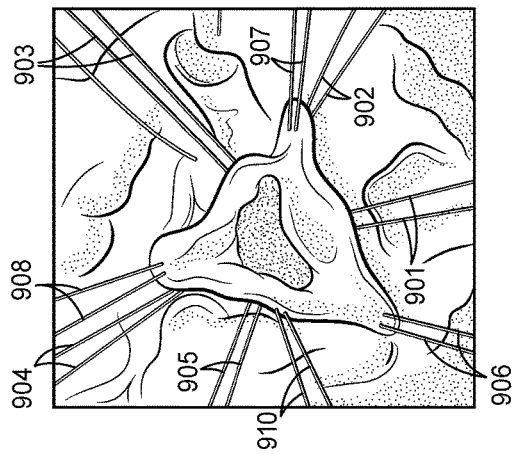
FIGS. 16A-16E in perspective views illustrate surgical steps associated with a valve sparing surgical procedure employing the annuloplasty ring of FIG. 1 and ring holder of FIG. 5 according to the principles of the present invention.
Figure 16B:
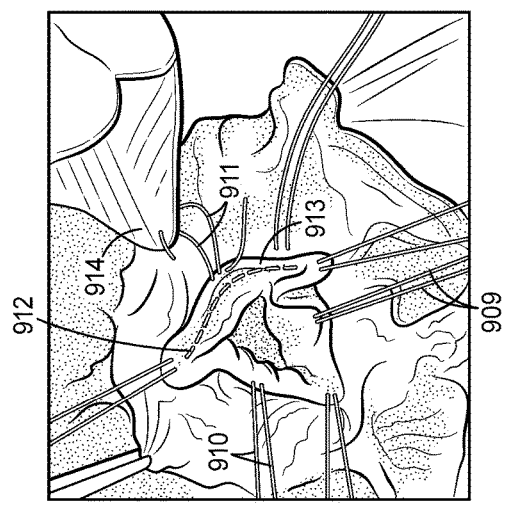
Figure 16C:
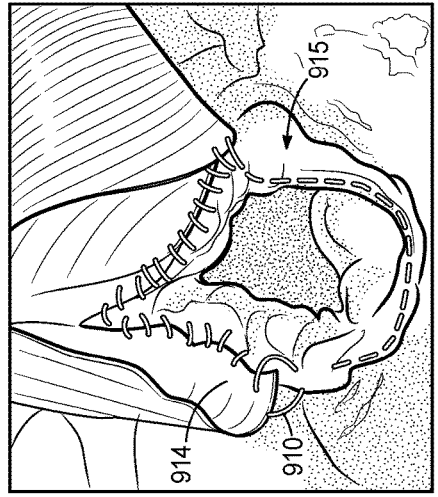
Figure 16D:
Figure 16E:
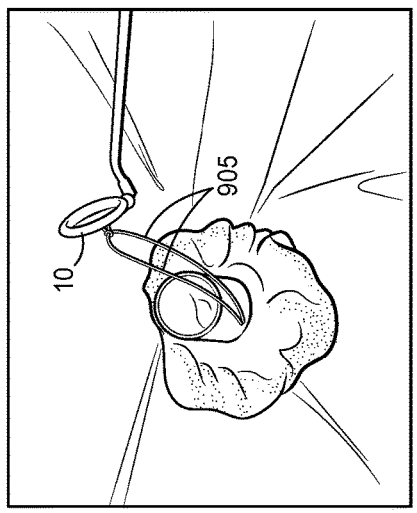
Figure 17A:
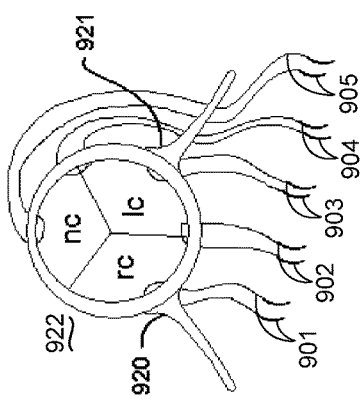
FIGS. 17A-17C illustrate the implantation steps of a split aortic annuloplasty ring in a leaflet valve sparing surgery whereby the native aortic root has been preserved.
Figure 17C:
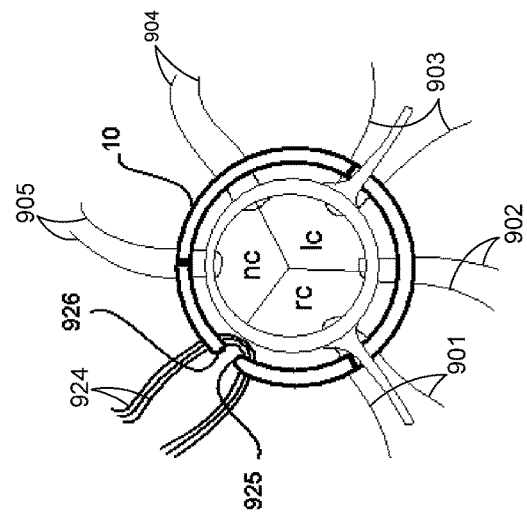
Figure 17B:
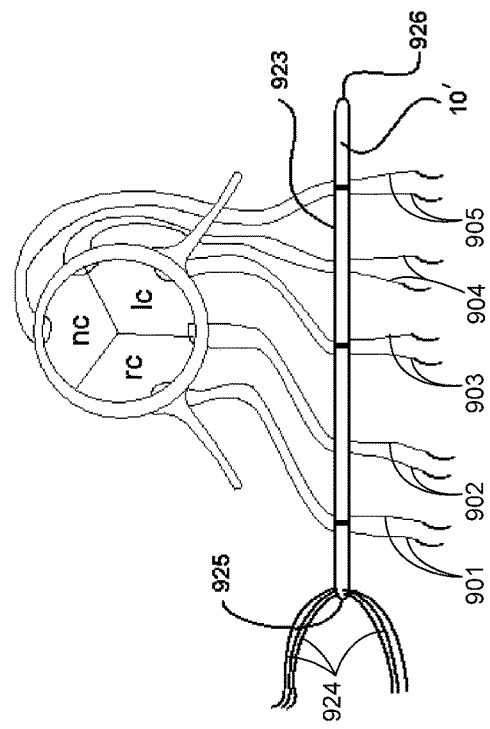

During aortic valve sparing surgery to preserve the native leaflets of the patient, it is convenient to implant the proposed annuloplasty ring 10 over the diseased aortic root AR in the diastolic configuration (see FIGS. 14C and 16D). Implanting the ring 10 as such, advantageously allows surgeon to assess leaflet coaption prior to closing aortotomy incision in ascending aorta. In the event of inadequate leaflet coaption, a different sized ring can be selected. Due to the elastic nature of the expandable ring 10, the free-state or pre-implantation diameter D0 (FIG. 3A) is smaller in size than the diastolic diameter D1. As such, a specially designed holder assembly 100 is described according to the present invention that would advantageously allow ring 10 to be implanted in its diastolic configuration over an aortic root AR to be surgically repaired (see FIG. 14C).

Holder assembly 100 consists of a handle member 105 and a detachable ring holding member or ring carrier or holder body 150 coupled thereto through mechanical interface or joint 106. Mechanical joint 106 preferably includes a detachable ball-and-socket interface which provides advantages in the context of aortic annuloplasty ring 10, but also in the context of other cardiac surgeries concerned with the implantation of a cardiac valve prosthesis engaged with a holder body. Alternatively, other types of less versatile mechanical joints may be used in lieu of joint 106 including a threaded fitting connection, an expanding collet, or any other like demountable mechanical coupling permitting handle 105 to be advantageously mounted to and demounted from ring holding member 150 during the surgical procedure.

Figure 5:
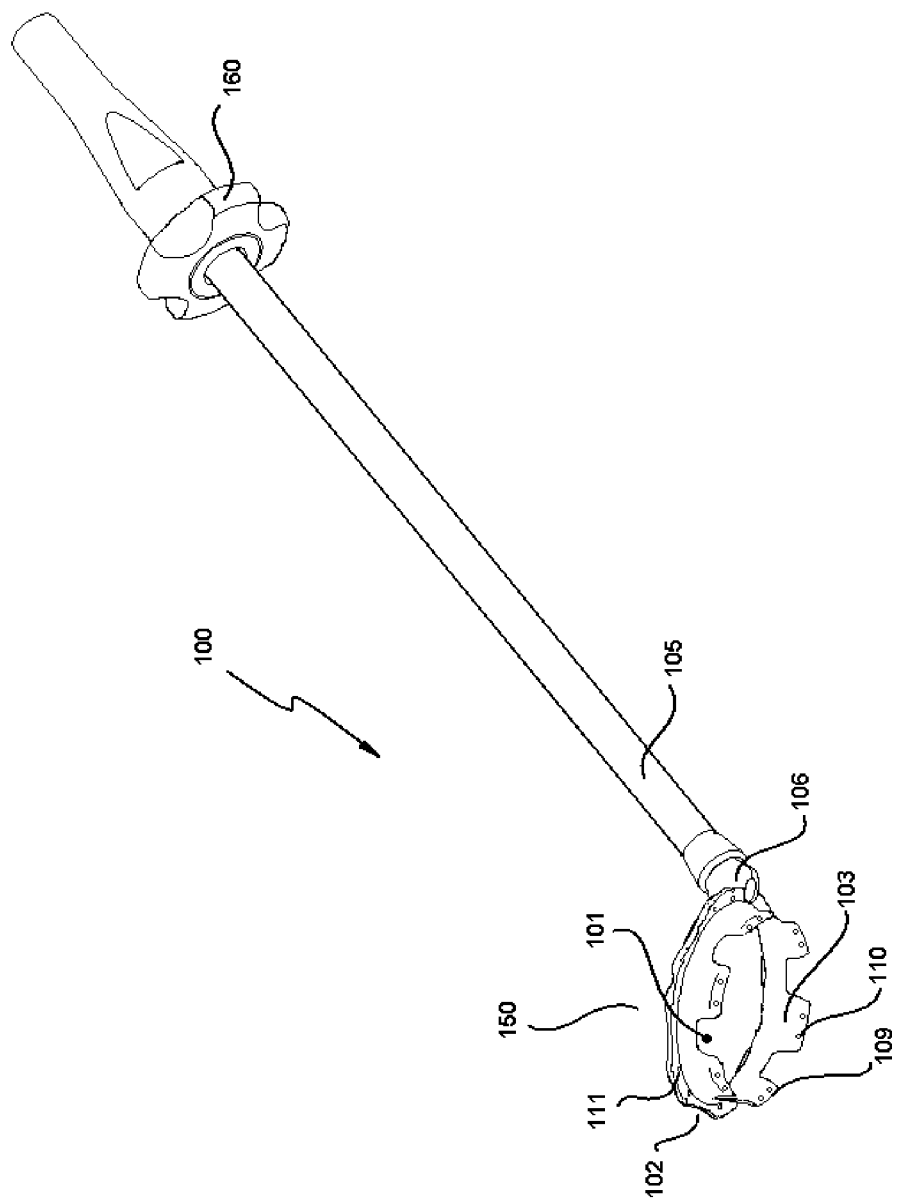
FIG. 5 in a perspective view illustrates an annuloplasty ring holder that may be advantageously used to implant the annuloplasty ring of FIG. 1 according to the present invention.
Figure 7:
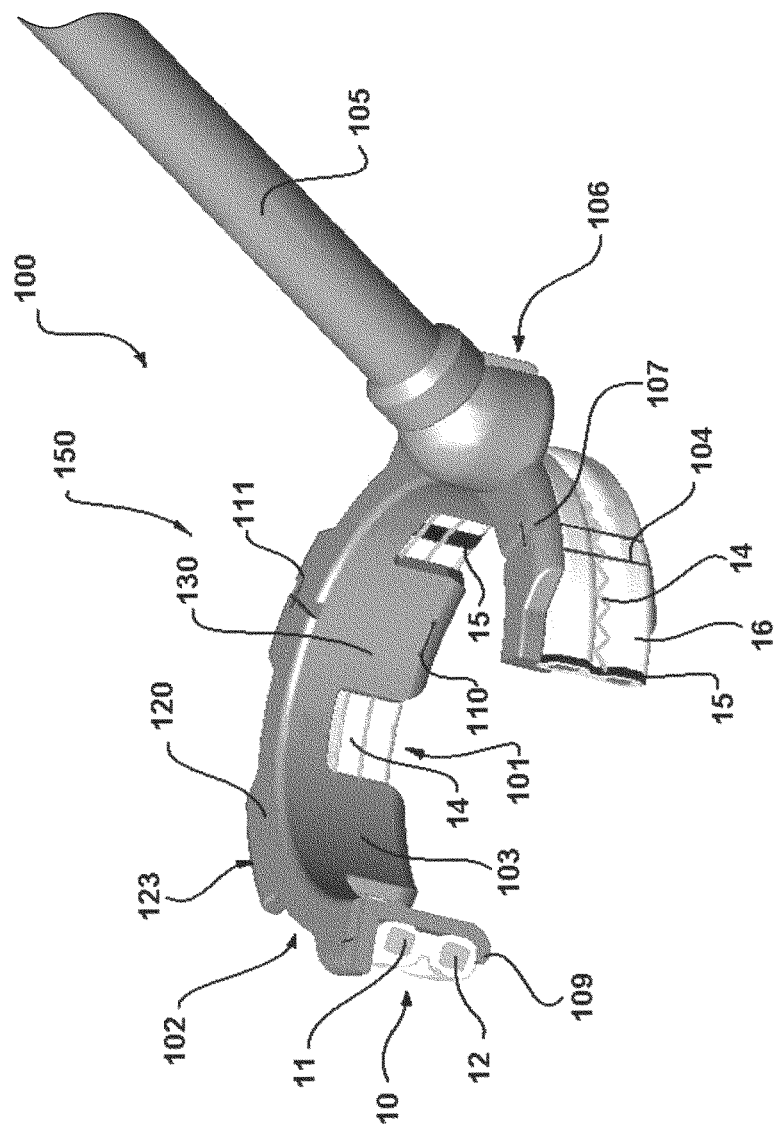
FIG. 7 in a perspective cutaway view illustrates the annuloplasty ring holder of FIG. 5 with the annuloplasty ring of FIG. 1 mounted thereto according to the present invention.

Referring to FIGS. 5-7, detachable ring holding member 150 consists of a top face or flange portion 120 and a cylindrical surface 130. Flange 120 is configured with a plurality of scallops 102, and cylindrical surface 130 is preferably configured with an equal number of suture access apertures or windows or slots 101 substantially angularly aligned with said scallops 102. As illustrated, holder body 150 is configured with five slots 101 and five scallops 102 (based on a pattern of six equally spaced) to reflect the proposed method of suturing ring 10 to the aortic root (five U-stitch sutures) as will be described in greater detail below. Other suturing arrays are also possible, depending on the suturing method employed and the number of fixation sutures placed. The holder body 150 may be also configured for alternate methods of ring fixation such as for instance stapling or use of shape memory clips such as U-Clips™ provided by Coalescent Surgical Inc.

As illustrated in FIG. 6, ring 10 is kept in its diastolic diameter D1 by being stretched from its pre-implantation diameter D0 and fit over cylindrical surface 130 and tangs 103. In addition, ring 10 is trapped axially between flange 120 (and lugs 123 extending outwardly therefrom) and bent terminal ends 109 extend outwardly from ends of tangs 103. During manipulation of the holder assembly 100 in the surgical procedure, a retaining means in the nature of a plurality of ring retaining sutures 104 (three as illustrated in FIG. 7) serve to secure ring 10 to holding member 150. Each of the retaining sutures 104 is threaded though a pair of holes 111 in lug 123 and also through a pair of cooperating holes 110 in tang 103 to form a continuous loop. This is one exemplary method of ring retention on holding member 150, and it is understood that other methods that hold ring 10 to holder body 150 during the implantation procedure are possible, such alternate ring retaining methods also being removable or releasable or severable to liberate the ring 10 cut from the holder body after said ring has been attached to the native aortic root. Scallops or recesses 102 advantageously provide recesses for the surgeon's finger when tying down the five U-stitch sutures that will anchor annuloplasty ring 10 to the aortic root. Each of the U-stitch sutures is preferably placed from the inside of ring 10 (through access slots 101 in suturing zone 14) and tied on the outside of ring 10 within suturing zone 14.

To detach ring-holding member 150 from annuloplasty ring 10 after implantation of said ring over diseased aortic root, the surgeon severs ring-retaining sutures 104 by passing a scalpel blade along depression of groove 107. Once all the retaining sutures 104 have been cut, and ring 10 is secured to aortic root by tying down the plurality of U-stitch sutures, holding member 150 is removed by pulling it upwardly away from aortic root generally in the direction of blood flow through the aortic root. An important design consideration is to configure cylindrical surface 130, and more importantly tangs 103 as thin as possible to facilitate disassembly of ring 10 from holding member 150. Tangs 103 may be shortened or removed if additional sutures to hold ring to holder body are used, or additional windings of said sutures are placed around the ring and holder body.

Alternatively, retaining means for ring onto holder may be retaining clips, or a pivoting leaf on the holder or other releasable like means that can be cut or disengaged to liberate ring from its holder Annuloplasty ring 10 is provided sterile and ready for implantation in a variety of classified sizes to cater to the different patient anatomies. For example, ring 10 may be provided in D1 sizes of 25 mm, 27 mm, 29 mm, 31 mm and 33 mm. Accordingly, ring 10 is preferably mounted to detachable ring-holding member 150, which is also provided sterile and packaged together with ring 10. The ring-holding member 150 may be formed using any appropriate manufacturing technique including molding, such as preferably injection molding, or it may be machined either as a single piece or as an assembly of components that are joined. Preferably, the holding member is fabricated using a biocompatible material such as polysulfone, polyphenylsulfone (such as Radel®), polyetheretherketone, acetal nitrile (such as Delrin®), polytetrafluoroethylene (PTFE), or any other suitable biocompatible material capable of resisting the loads imparted from the annuloplasty ring mounted on the holding member 150 in its diastolic configuration.

Handle member 105 may also be provided sterile or provided as a reusable, re-sterilizable implement made from surgical-grade metal alloys.

In reference to FIGS. 8A-8H, a coordinate reference system X-Y-Z has been drawn to more clearly describe the relationship between the figures and components of the holder 450 and handle 405 cooperating at the ball-and-socket joint or interface 406. Plane X-Y defines a prosthesis plane 451 located generally perpendicular to the direction of blood flow through prosthesis or annuloplasty ring 10 when it is implanted in the patient's body. When a prosthesis is mounted to its holder body, for instance ring 10 to holder 450, said prosthesis plane 451 also serves to define a holder plane 452.

Ball or domed protrusion or spherical boss 453 is preferably formed as an integral part of holder body 450. It may be molded by plastic injection as a protrusion preferably extending above top planar surface 454 so as to allow unencumbered pivoting of handle 405 relative to holder 450. Also, such a boss arrangement does not interfere with annuloplasty ring 10 which is mounted below top planar surface 454. As well, such an arrangement reduces the likelihood of the boss 453 and handle 405 distal end contacting the native aortic tissue NAR during implantation of ring 10.

Spherical boss 453 is provided with a spherical surface 455 which is configured and sized to cooperate with socket surface 456 on distal end 457 of handle 405 to allow articulation therebetween and pivoting of holder 450 relative to handle 405 at ball-and-socket joint 406.

Figure 8C:
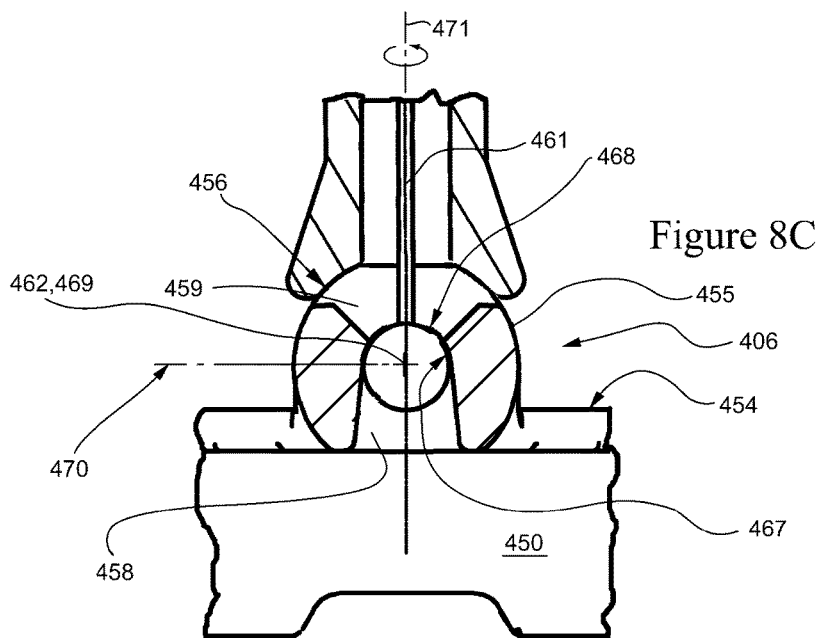

Spherical boss 453 is interrupted by a tapered hole or passage 458 extending toward the center of said boss. A countersunk depression 459 also extending toward the center of said boss from a diametrically opposite side. Tapered passage 458 and countersink 459 meet and are aligned, as illustrated in FIG. 8C, along the Z-direction.

Figure 8D:
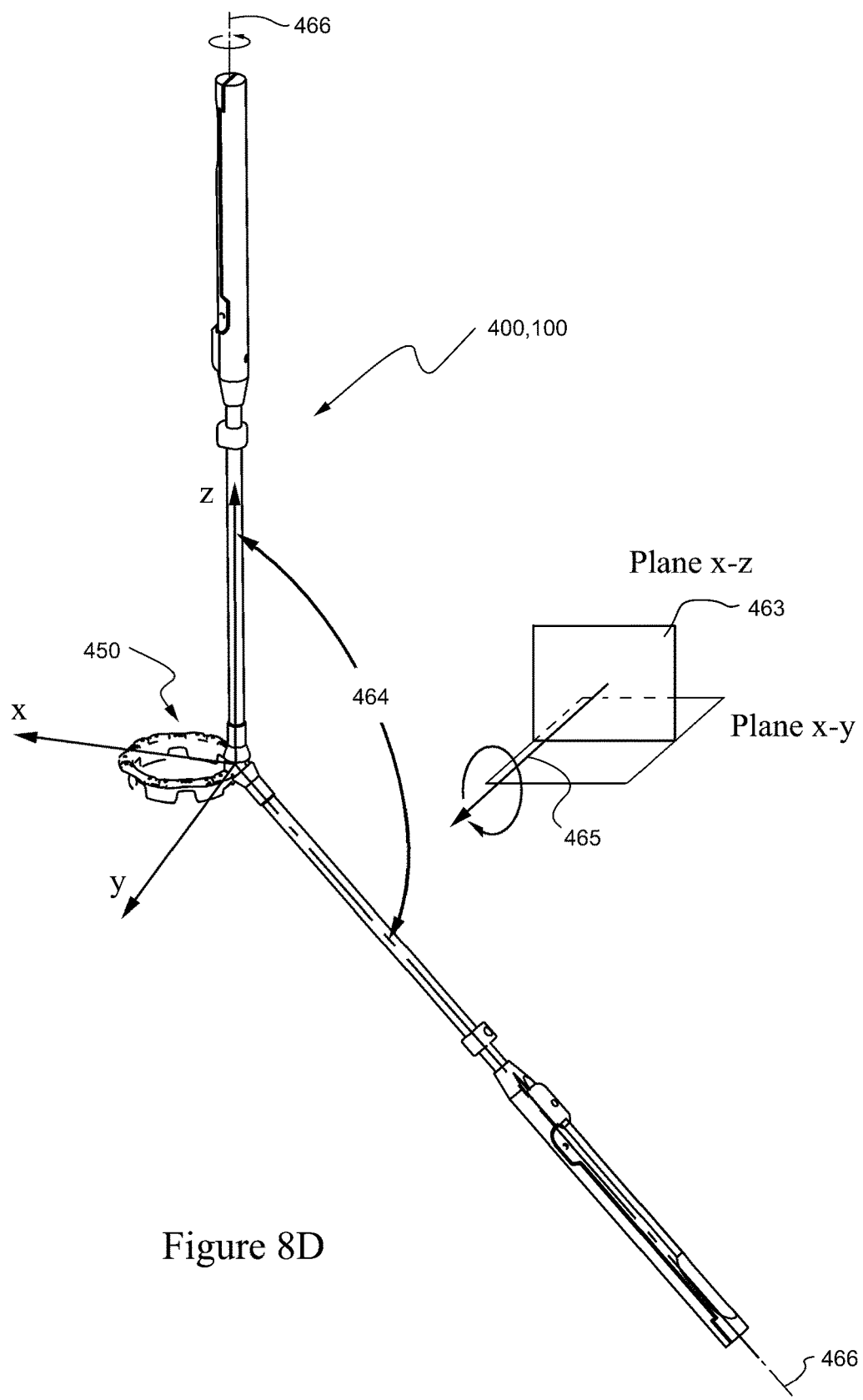

Spherical boss 453 is interrupted by slot or passage 460 which also intercepts tapered hole 458 and countersink 459. As illustrated in FIG. 8A, said slot is aligned with the X axis and extends along Plane X-Z. Slot 460 is sized to allow cable 461 to move and pivot freely therethrough as handle 405 pivots within a first pivot plane generally aligned with slot 460 and extending through center point 462 of spherical boss 453. As illustrated in FIGS. 8B and 8D, said first pivot plane 463 is Plane X-Z. As illustrated in FIG. 8D, a ball-and-socket arrangement 406 as described above will allow pivoting of handle 405 relative to holder 450 within an exemplary range 464 of 120 degrees+/−30 degrees. This is equivalent to holder 450 pivoting relative to handle 405 with the same exemplary range, said pivoting occurring about a first pivot axis 465 that is perpendicular to longitudinal axis 466 of the handle 405. It is understood that slot 460 can have a different orientation with respect to boss 453 and holder plane 452 than the orientation illustrated.

Tapered hole 458 provides an abutment or seat or shoulder 467 for terminal ball end 468 formed on end of cable 461. To engage holder 450 on handle 405, terminal ball end 468 is inserted through passage or opening 458 while cable 461 simultaneously enters within slot 460. Tapered hole 458 is configured and sized to allow ball end 468 to be inserted sufficiently until center point 469 of ball 468 is coincident with center point 462 of spherical boss 453. The tapered surface 467 of tapered hole 458 extending above the centerline 470 of boss 453 and ball 468 in FIG. 8C acts as a seat or socket for ball end 468. Tapered surface 467 may be a spherical or a conical surface. Minimum dimension of tapered hole 458 is smaller than diameter of ball end 468 to prevent said ball end from slipping into countersink 459.

Boss 453 simultaneously acts as a "ball member" for cooperating socket 456 in handle distal end 457, and a "socket member" for cooperating ball 468 on cable 461 distal end. As such, the arrangement 406 advantageously provides a pair of concentric ball-and-socket interfaces acting in parallel, to allow the range of free orientation between holder 450 and handle 405. Such an arrangement also provides for the free rotation of the holder 450 relative to the handle 405 about the centerline axis 471 of translating member or cable 461 (see FIGS. 8C and 8F). This rotation of holder 450 about centerline 471 can occur over an angular range of 360 degrees, provided ball end 468 remains in engagement with seat portion 467 of tapered hole 458. In the embodiment illustrated in FIGS. 8A-8H, centerline 471 is coincident with longitudinal axis 466 of handle 405.

Other variants for a tapered hole are also possible without departing from the invention. For instance, tapered hole 458 may be replaced by a counterbored hole provided the shoulder of said counterbore locates ball 468 within spherical boss 453 such that centerpoints 462, 469 of boss 453 and ball 468 are substantially coincident.

Figure 8E:
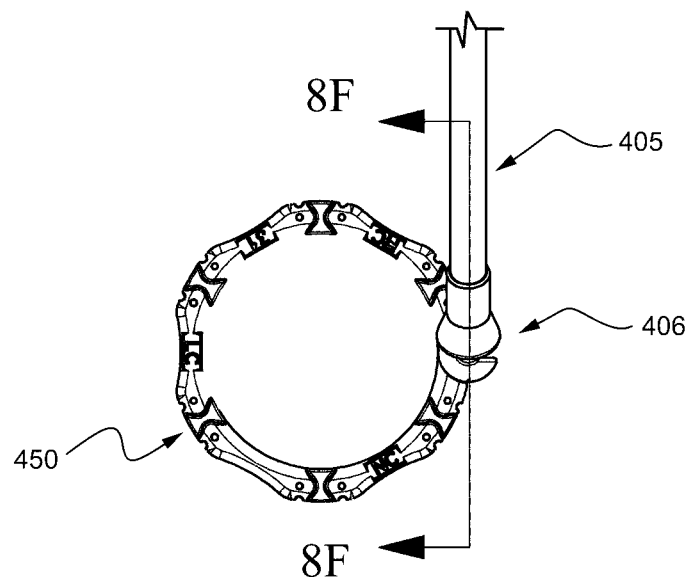
Figure 8F:
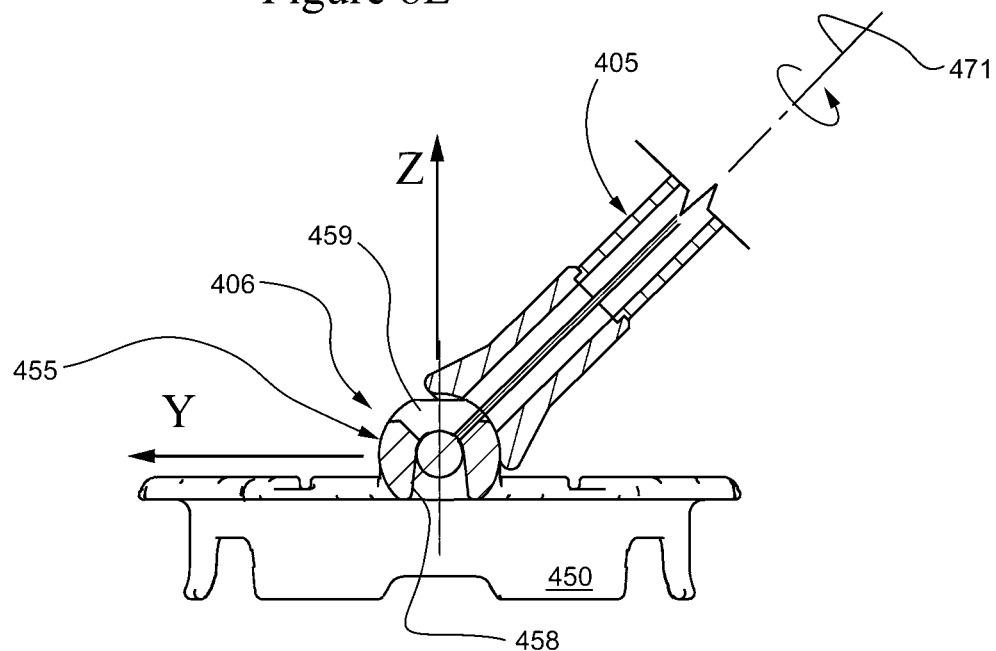
Figure 8G:
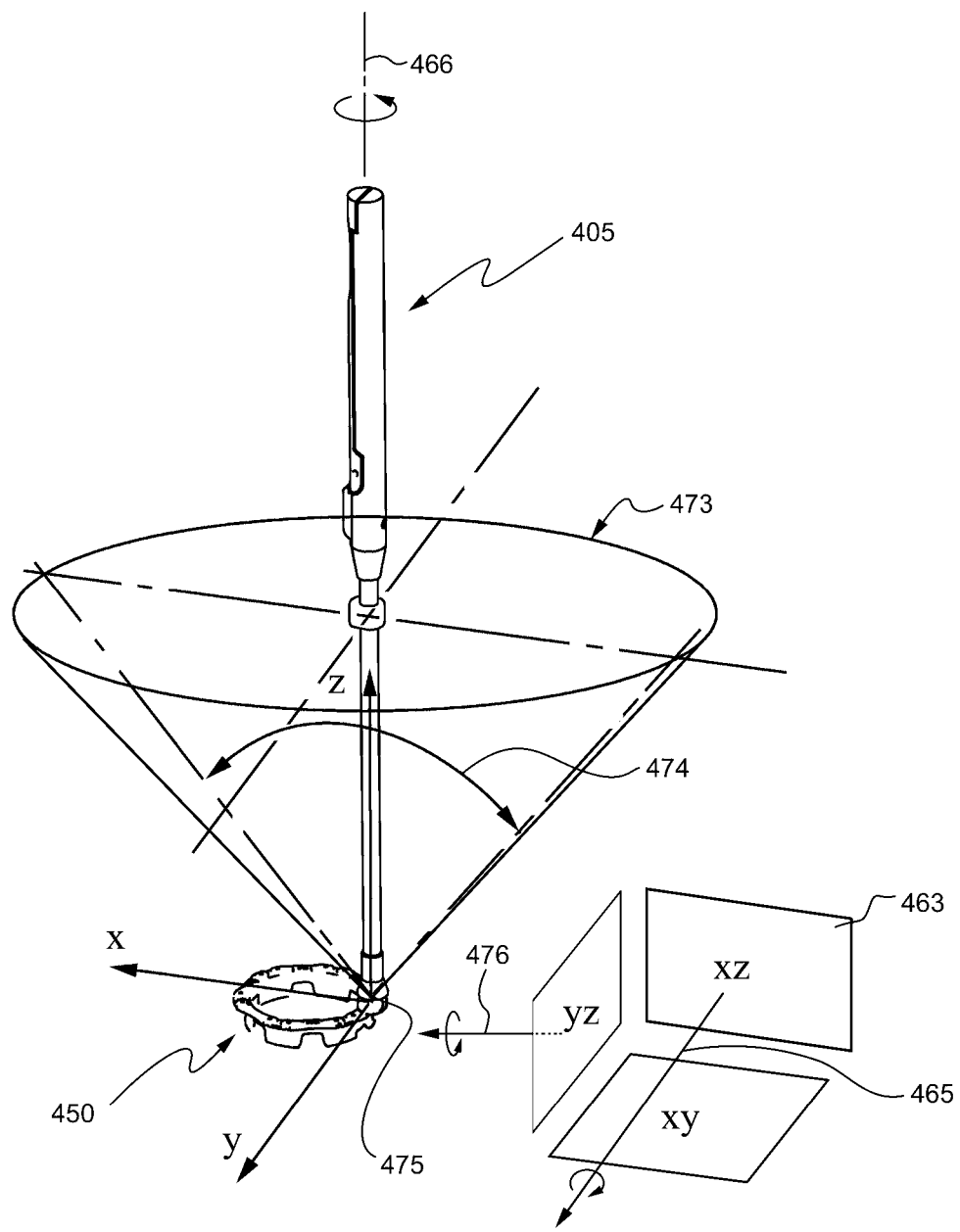

With reference to FIGS. 8E and 8F, the range of motion or possible orientations that the ball-and-socket arrangement can provide in any other plane other than plane X-Z (i.e. a first pivot plane 463) will now be described. In plane Y-Z as illustrated in FIG. 8F, the pivoting range of the holder 450 relative to the handle 405 is determined by the included angle of the countersink depression 459 and the difference in diameter of the cable 461 relative to the diameter of ball 468. The range of articulation in plane X-Z translates to a conical volume 473 as illustrated in FIG. 8G, within which the handle 405 can free pivot relative to holder 450. A ball-and-socket arrangement 406 as described above will allow pivoting of handle 405 relative to holder 450 within an exemplary range of orientations of 90 degrees+/−15 degrees. This said exemplary range of orientations being defined by a conical volume having an inclusive cone angle 474 and a vertex 475 at the coupling point 462 between handle member 405 and holder body 450, with the handle member longitudinal axis 466 being contained within said conical volume 473 when said handle member 405 is movable within said free range of orientations. This is equivalent to the holder 450 pivoting relative to handle 405 with the same exemplary range. As such, the ball-and-socket arrangement 406 allows pivoting of holder body 450 about a second pivoting axis 476, said second pivoting axis being perpendicular to each of said first pivoting axis 465 and handle member longitudinal axis 466.

As illustrated in FIG. 8G, boss 453 has been configured to yield a conical volume 473 that is normal to the plane X-Y (i.e. or the prosthesis plane 451 or holder plane 452). It is understood that varying the orientation of said boss relative to plane X-Y, different from that which is illustrated, may result in a conical volume which is not perpendicular or normal to plane X-Y. As such, a different range of orientations of handle 405 relative to holder plane 452 may be provided.

Those skilled in the art will appreciate that the ranges of orientation (parameters of conical volume 473 in FIG. 8G) may be modified by varying any one or a combination of the geometrical relationships such as the difference between cable diameter 461 and ball end diameter 468, the difference between cable diameter 468 and minimum tapered hole 458 diameter, the included angle of countersink depression 459.

Figure 8H:
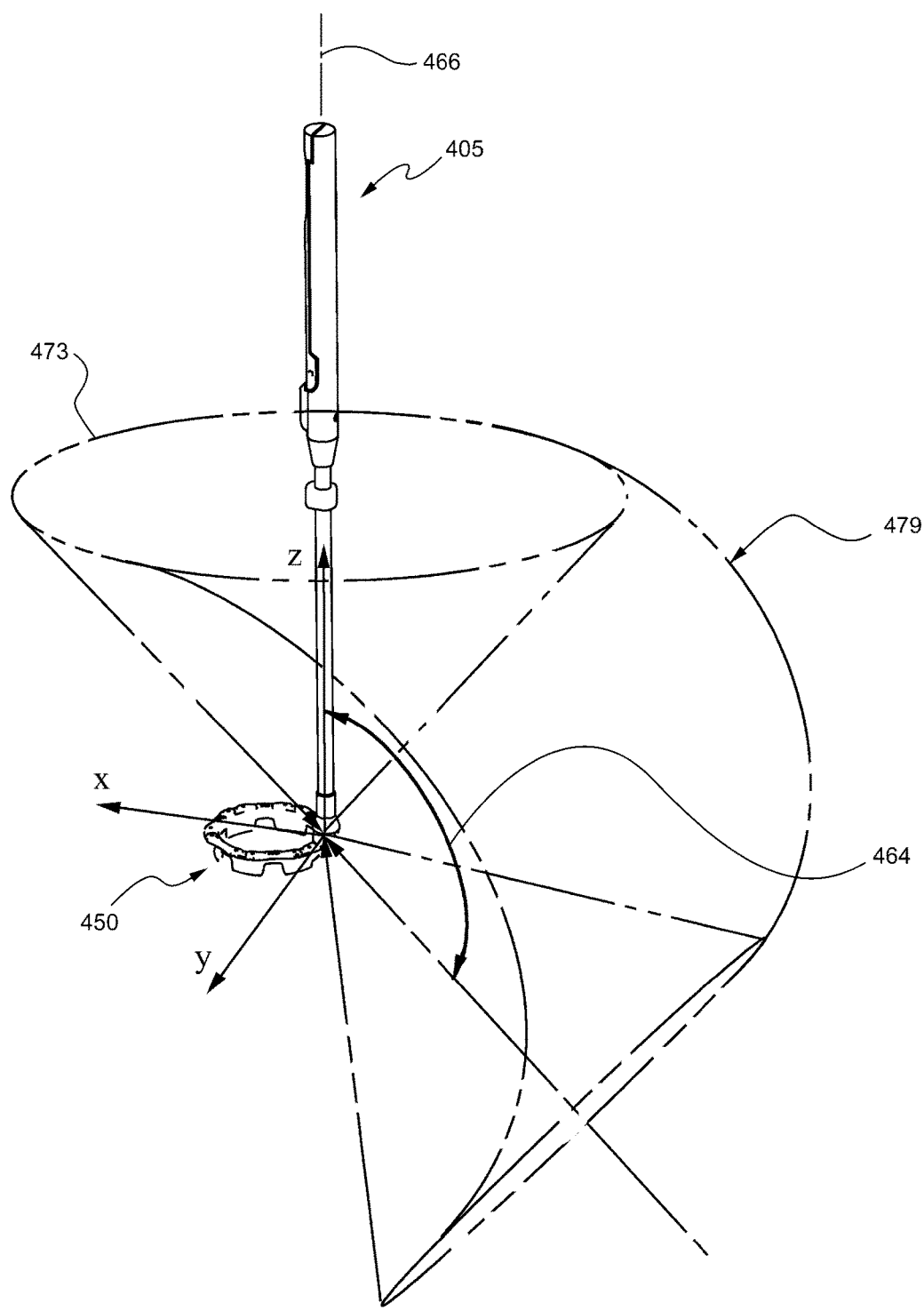

FIG. 8H illustrates the full or complete range of orientations and rotations 479 between holder body 450 and handle member 405, as provided by one exemplary embodiment of the ball-and-socket arrangement 406. FIG. 8H illustrates that the conical volume 473 described in FIG. 8G can be angularly swept through an angle 464, as cable 461 is able to move through slot 460 along plane 463, and while boss spherical surface 455 and socket surface 456 remain in articulating contact.

Within the full range of orientations and rotations that are possible between the holder and handle by virtue of ball-and-socket arrangement 406, holder 450 can be secured or locked in a desired orientation or position, within said range, through the actuation of translating member or cable 461. Cable 461 may be retracted inwardly relative to seat 456 in handle 405, and as such draw into progressively increasing frictional contact cooperating ball-and-socket surfaces 455, 456 (between holder and handle), and simultaneously cooperating ball-and-socket surfaces 468, 467 (between actuator cable and tapered hole in boss). The amount of frictional contact provided by actuating cable 461 can be determined by the design of actuator means 480 described below. A suitable surface texture treatment can also be advantageously provided between cooperating ball-and-socket surfaces either to enhance friction therebetween and promote improved locking when actuator 480 is in a locked configuration, or to reduce friction therebetween so as to facilitate ease of orientation of holder relative to handle when actuator 480 is in an unlocked configuration.

A pivotingly coupled holder to handle embodiment through a ball-and-socket joint 406, offers many distinct and unique advantages over the prior art. These include a relatively compact and simple to fabricate functional joint with component interfaces that are easy to clean and sterilize. The enhanced range of orientations and rotations between handle and holder provide great versatility in tailoring the surgical set-up to suit the specific patient anatomy, the anatomic routing of the holder as a function of the surgical approach or access, and the surgeon individual work preference. The ability to selectively and securely lock the holder relative to the handle in a desired orientation provides a safe method of utilization. The ability to releasably connect the holder to the handle allows the handle to be advantageously decoupled from the holder during a phase of the surgical intervention and reconnected during a subsequent phase. As well a releasable connection allows for rapid changeovers between different holder sizes and/or different sizing implements with a common single universal handle.

Figure 9A:
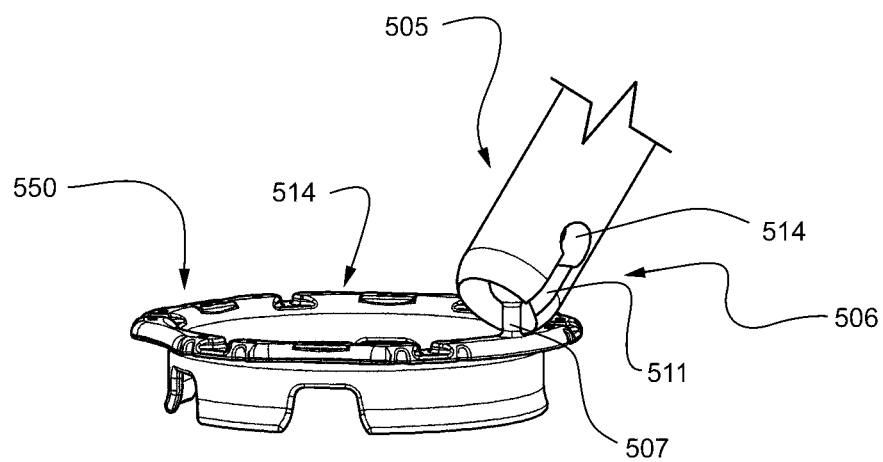
FIGS. 9A-9B illustrate a variant embodiment for a ball-and-socket arrangement 506 between holder body 550 and handle member 505.
Figure 9B:
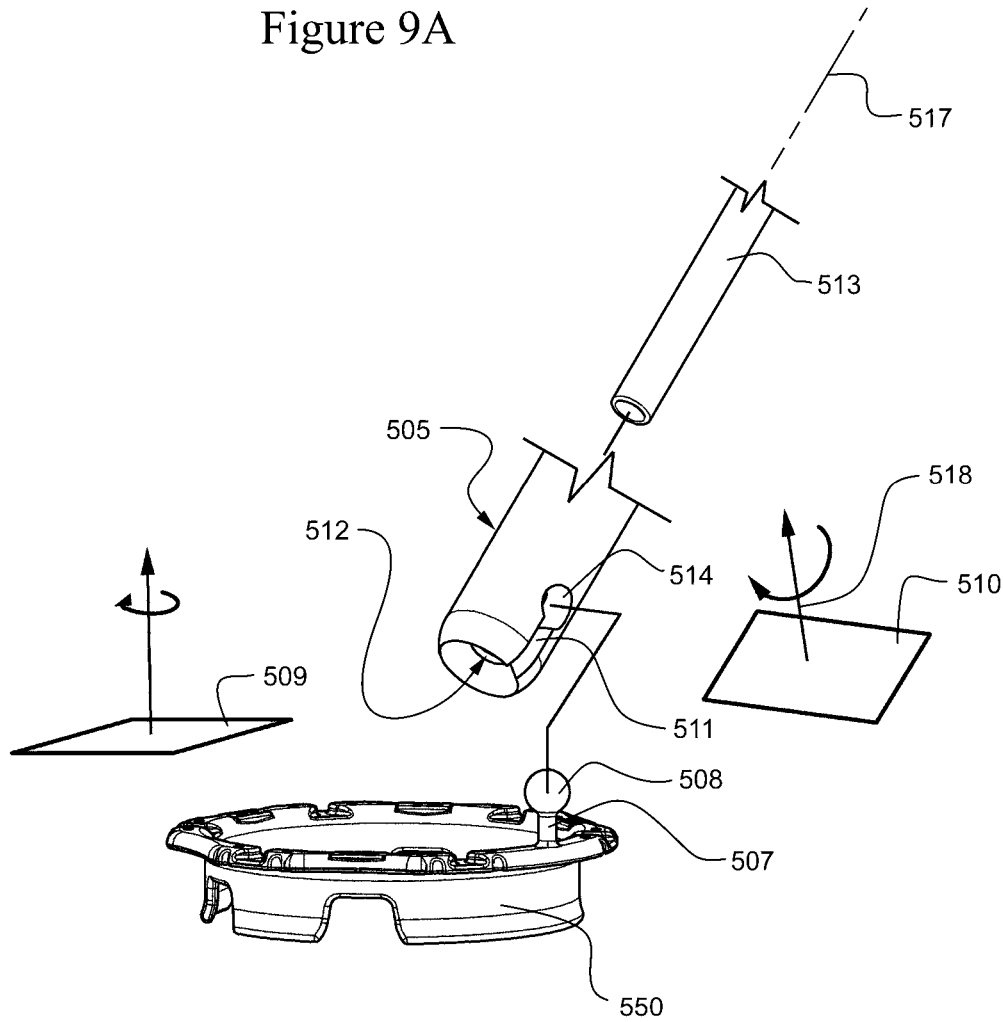

FIG. 9 illustrates a variant ball-and-socket interface 506 between handle 505 and holder 550. Holder 550 defines a holder plane 509. In this embodiment, holder 550 is configured with an upstanding post 507 extending away from top surface 514 of holder 550. Post 507 terminated in a spherical ball end 508. Handle 505 is provided with a gate or entryway or passage 514 to allow ball 508 to engage seat or socket 512 configured within hollow cavity in handle 505. Socket 512 is provided with a spherical or conical surface that mates and cooperates with spherical surface of ball 508 thereby permitting relative articulation therebetween. Said surfaces also cooperate to lock the orientation of said holder relative to said handle when they are urged into frictional contact by translating member 513.

When post is aligned with slot 511 in handle 505, the holder can articulate or pivot within a first pivot plane 510, said first pivot plane extends through said slot 511 and contains the center point of ball 508. Pivoting within said first plane is about axis 518 which is perpendicular to axis 517. When ball-and-socket arrangement 506 is unlocked, the holder can also rotate freely about the centerline axis 517 of member 513, and can also pivot about a second pivot axis that is perpendicular to both handle axis 517 and first pivoting axis 518. Unlike the ball-and-socket arrangement 406, arrangement 506 is a single ball-and-socket arrangement and offers less range of orientation between holder and handle. It is also relatively more difficult to release holder body 550 from handle 505 given the lateral insertion of ball 508 in entryway or slot 514.

Unlike preferred embodiment of FIG. 8A-8H, translating member 516 acts in compression to apply locking force to ball-and-socket interface 506. Translating member or rod 506 can be actuated by the same actuator illustrated in FIG. 10, and similar actuator as illustrated in FIG. 11A.

Figure 10:
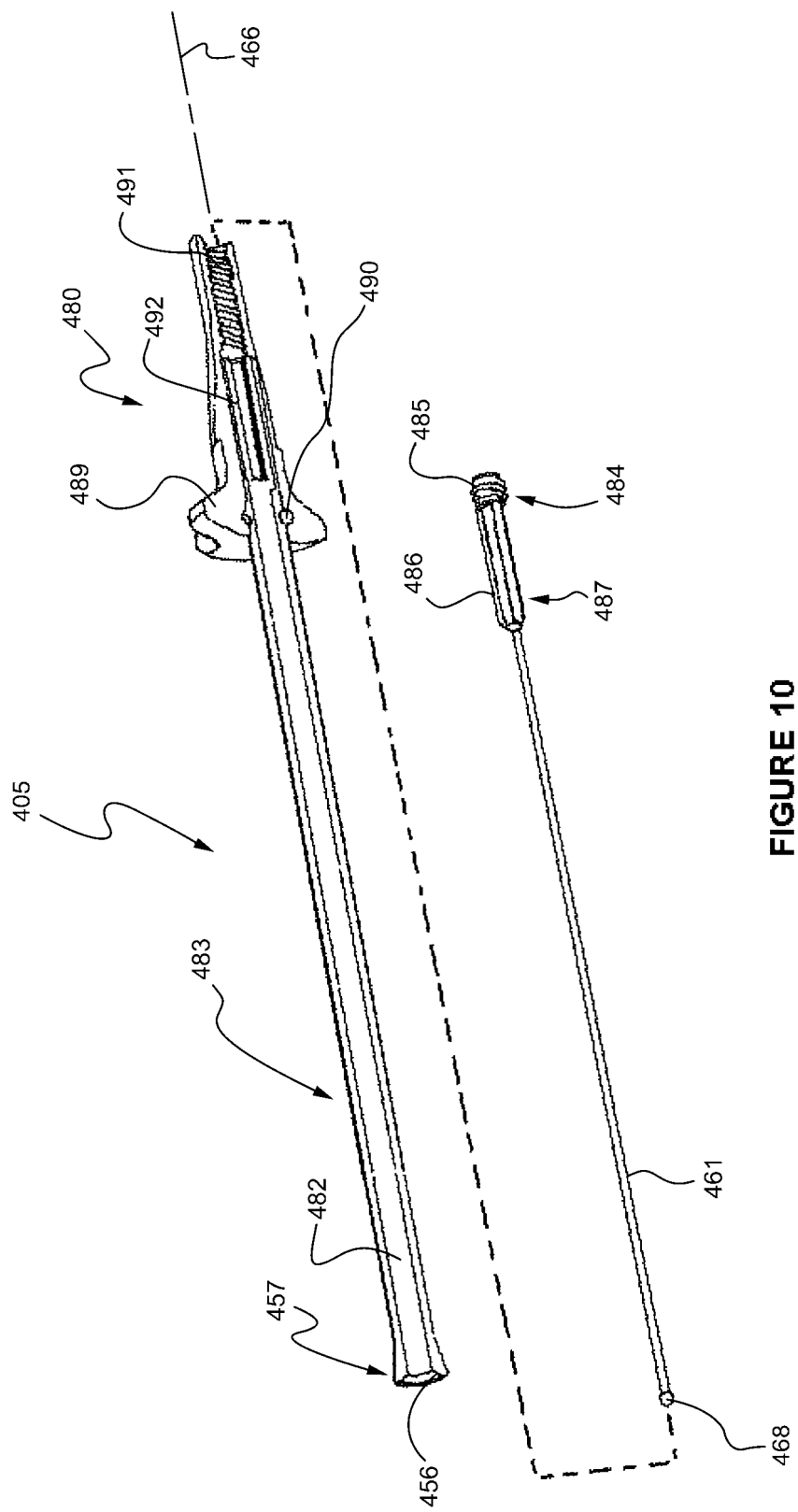
FIG. 10 illustrates a handle member 405 having an actuator 480 according to the present invention.

As illustrated in FIG. 10, handle member 405 is generally elongate along a longitudinal axis 466 and has a distal end 457 for connection to a holder body 450 and a proximal end 481 that is adapted to be gripped by the surgeon during the surgical intervention.

Handle distal end 457 is configured and sized with a socket or seat 456 to mate with cooperating boss 453 on holder body. Seat 456 is provided with a concave spherical surface, or a conical depression, or any other surface suitable to mate with boss 453 that allows articulation therebetween but also locking therebetween when a contact pressure is exerted between said seat and boss.

The seat communicates with a channel or passageway 482 that extends longitudinally through said handle body 483 between said distal end and proximal end. Channel 482 is sized to house and allow translation therewithin of a translating member. Translating member can be a rod, shaft or preferably a cable 461. Cable 461 is provided at its distal end with a terminal ball or spherical end 468 that is configured to be insertable in tapered hole 458 and interface with tapered surface 467 in a manner describe above. Terminal ball end 468 is greater in diameter than the cross-sectional dimension of the cable 461. At its proximal end 484, said cable is provided with a threaded interface 485 and anti-rotation key 486. Preferably, thread 485 and key 486 are formed on a common fitting 487 that is attached to cable 461 through plastic injection overmolding, or mechanically joined to said cable in a permanent manner. Cable 461 is insertable through proximal open end 481 of handle and is preferably demountable to allow effective cleaning of passageway 482 after surgical use. Cable 461 may be provided sterile as a single use component.

Proximal end 481 of handle is provided with a proximal actuator or actuation member 480 in the nature of a threaded control knob 489. Knob 489 is rotatingly engaged to handle proximal end 481 through an axial retention member, such as bearing 490, which axially retains said knob but allows it to rotate about handle or cable axis 466. Knob is provided with an internal thread 491 configured to mate with cable external thread 485. Handle body 483 is configured at it proximal free end with an anti-rotation slot or keyway 492. Said keyway is located intermediate to said knob thread 491 and bearing 490 when knob 489 is coupled to handle 405. When cable is inserted through handle passageway 482, key 486 will first engage keyway 492 and thread 485 will subsequently engage thread 491. As such, a rotation applied to knob 489 will result in cable 461 translating through handle 405 since anti-rotation keyway 492 allows sliding engagement of key 486 but no rotation of cable 461.

Range of translational motion allows cable ball end 468 to extend sufficiently outwardly from seat 456 so as to engage tapered hole 458 in holder 450. Then, as said cable is retracted inwardly, the cooperating surfaces of mechanical joint 406 come into light contact allowing the relative articulation and rotation therebetween of the holder relative to handle. As cable 461 is retracted further still, the contact force between cooperating surfaces of joint 406 progressively increases and the resulting friction at joint 406 securely locks the joint and the position of holder 450 relative to handle 405.

As such, the actuator 480 is operable within a first actuation range to selectively release and engage the holder from the handle. Within a second actuation range, as cable 461 is retracted further into the handle passageway 482, the actuator 480 is also operable to selectively secure or lock the orientation between holder and handle at mechanical joint 406. By virtue of the threaded arrangement between actuator knob 489 and translating actuating member or cable 461, the surgeon may incrementally vary the contact forces and friction at mechanical joint 406 so as to set precisely the amount of resistance desired to overcome same and reorient the holder relative to the handle.

FIG. 11A-11B illustrate an alternate embodiment for a handle member 605 having a variant actuator or actuation member 680 in the nature of a lever member 689.

Handle member 605 is provided with a translating member 661 having a terminal ball end 668 at a distal end, and a clevis member 626 at the proximal end configured for rotating engagement with transfer linkage 630 at a first joint. Transfer linkage 630 is rotatingly connected to lever 689 through a second joint 623. Lever 689 is connected to handle proximal end 631 through a leaf spring member 624 which biases said lever into its open configuration 621 as illustrated in FIG. 11B, but allows said lever to pivot angularly about the end 631 of handle when said lever is depressed. In said open configuration, ball end 668 extends sufficiently outwardly from seat 656 to allow said ball to become engaged in tapered hole 458 of holder body 450.

When actuation lever 689 is depressed, angular rotation of said lever entrains a rotation of transfer linkage 630 towards said lever and translating motion of member 661 along way 625 that retracts ball end 668 towards seat 656. Continuing to depress lever 489 will laterally displace spring loaded latch 622 and result in lever being held in its closed configuration 620 (FIG. 11A) when said spring loaded latch 622 recoils over and above the lever 489. In said lever closed configuration, the ball 668 is sufficiently retracted towards seat 656 to effectuate the locking of holder relative to handle 605. To unlock the holder from the handle, either to reorient its position or to release it from the handle, latch 622 is overcome by surgeon, thereby liberating the lever 689 to resume its biased open configuration 621 of FIG. 11B. As such, actuator 680 is selectively operable between an open configuration 621 (FIG. 11B) allowing the holder to be coupled or decoupled from the handle, and permitting the free orientation of holder relative to handle, and a closed configuration 620 (FIG. 11A) securely locking the holder relative to handle.

Handle 605 is provided with a cleaning or flushing port 627 to allow proper cleaning of handle without removing translating member from handle body.

Figure 12A:
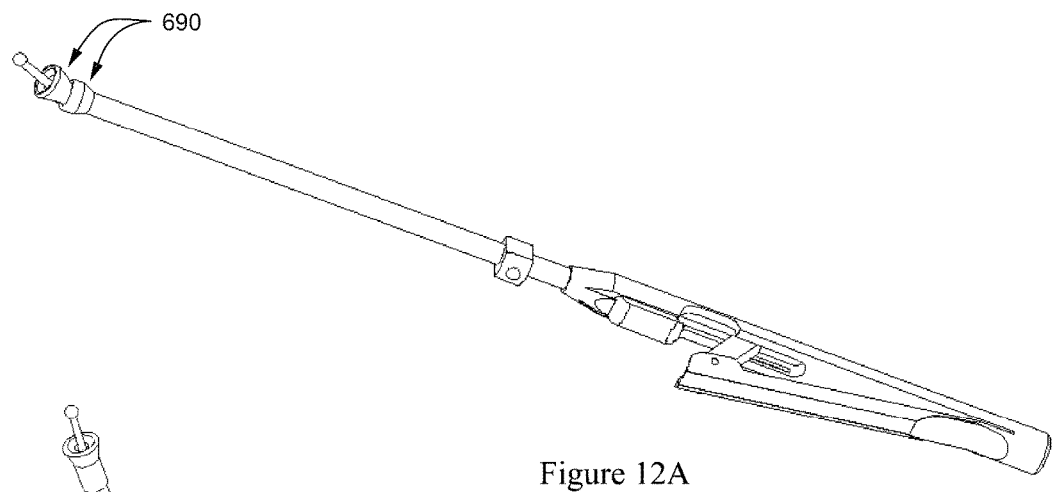
FIGS. 12A-12C illustrate further variants of the handle member 505 illustrated in FIG. 11A.

FIG. 12A illustrates a further variant of embodiment of FIG. 11 having an additional preferably non-detachable ball-and-socket joint 690, configured in series with the detachable ball-and-socket joint 406 between holder and handle. This additional joint 690 advantageously provides supplemental articulation range of the holder 450 relative to longitudinal axis 466 of handle, over the articulation range defined by conical volume 473 defined in FIG. 8G. Such an arrangement allows the articulation range to be increased without increasing the size of ball and socket arrangement 406 to obtain a larger conical volume 473.

Figure 12B:
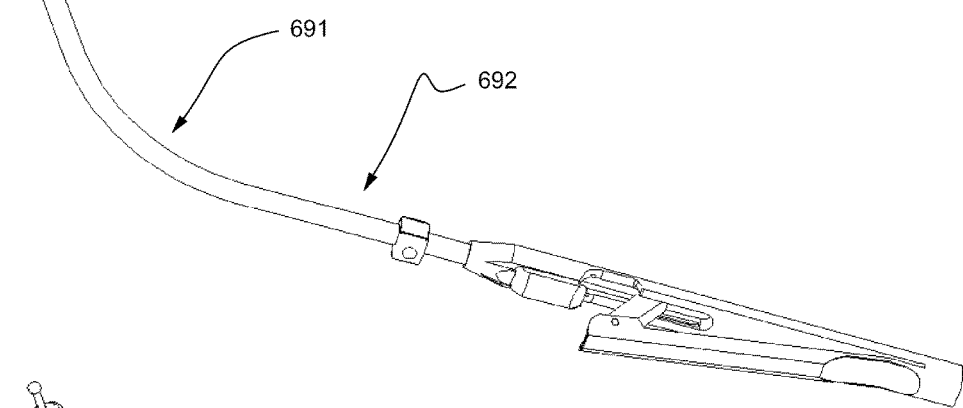

FIG. 12B illustrates yet a further variant of embodiment of FIG. 11 having a predetermined permanent bend 691 in handle 692. Such an arrangement may be advantageous in certain surgical approaches, for instance valve surgery performed by intercostal approach, where bend 691 provides a desired anatomic routing for the handle 692 that avoids certain body tissues while preserving variability in orientations between holder and handle at distal end thereof.

Figure 12C:
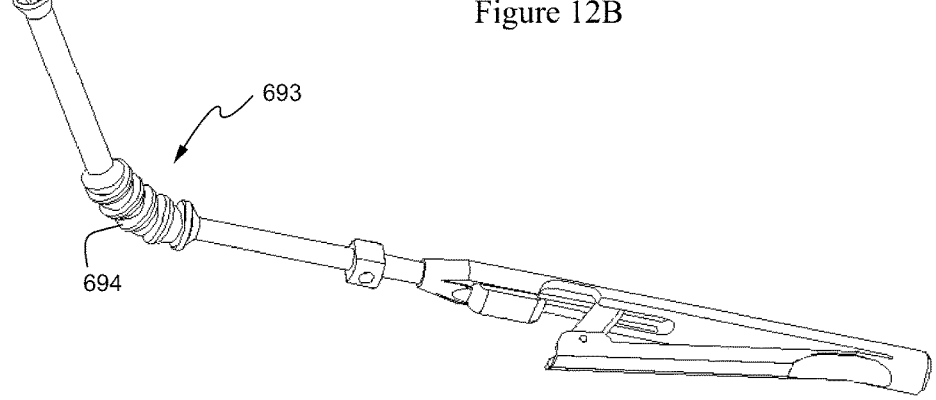

FIG. 12C illustrates yet a further variant of embodiment of FIG. 11 having an adjustable single or multiple complex bend 693 provided by a plurality of interconnected and cooperating sockets 694. Such an arrangement advantageously allows adjustability in the handle configuration depending on the desired anatomic routing or available surgical access in a given patient, or even to cater for surgeon preference.

Referring to FIGS. 14A-14D and 15A-15D, annuloplasty ring 10,10' is implanted on the outside surface of aortic root AR. Two examples of valve leaflet sparing surgeries are illustrated. FIGS. 14A-14D illustrate implantation of the proposed annuloplasty ring 10, in a plane located generally below (i.e. below the valve cusps or leaflets) or at the level of the aortic annulus, in a leaflet valve sparing procedure including resecting of an aneurysmal aortic root. As such, the diseased aortic root 10 is scalloped prior to implantation of annuloplasty ring 10 by surgically removing the diseased portion of aortic root that defines the Sinuses of Valsalva (i.e. located above the coronet-shaped aortic valve annulus ANN and generally below the plane of the sinotubular junction STJ) (see FIG. 14A). In this surgical procedure, a synthetic or prosthetic vascular conduit VC (i.e. as illustrated Gelweave™ by Vascutek) is used to replace the portion of diseased aortic root AR and ascending aorta that has been surgically resected. The vascular conduit VC is fashioned or scalloped by the surgeon to mate with the remaining scalloped portion of native aortic root SAR. The vascular conduit VC is attached to the scalloped aortic root SAR through suture line SL. Also in this procedure, the coronary buttons CB of the left and right coronary arteries are reattached to the vascular conduit VC, in the scalloped portion of vascular conduit VC that recreates neo-sinuses of Valsalva.

FIGS. 15A-15D illustrate implantation of the preferably two separate annuloplasty rings 10, 10', in an aortic valve sparing procedure that preserves both the native valve leaflets and native aortic root NAR, while resizing the aortic root in order to correct aortic insufficiency. In this procedure, one ring 10 is implanted at the base of the native aortic root NAR in a plane located generally below the aortic annulus (i.e. below the valve cusps or leaflets), and one ring 10' is implanted at the level of the sinotubular junction STJ. This procedure does not generally require the need for a synthetic or prosthetic vascular conduit. To avoid having to resect and re-attach the coronary buttons of the left and right coronary arteries, ring 10' placed at the base of the aortic root is preferably configured with a mechanical joint 169 to allow its insertion below the coronaries, without departing from the spirit of the present invention.

Figure 19A:
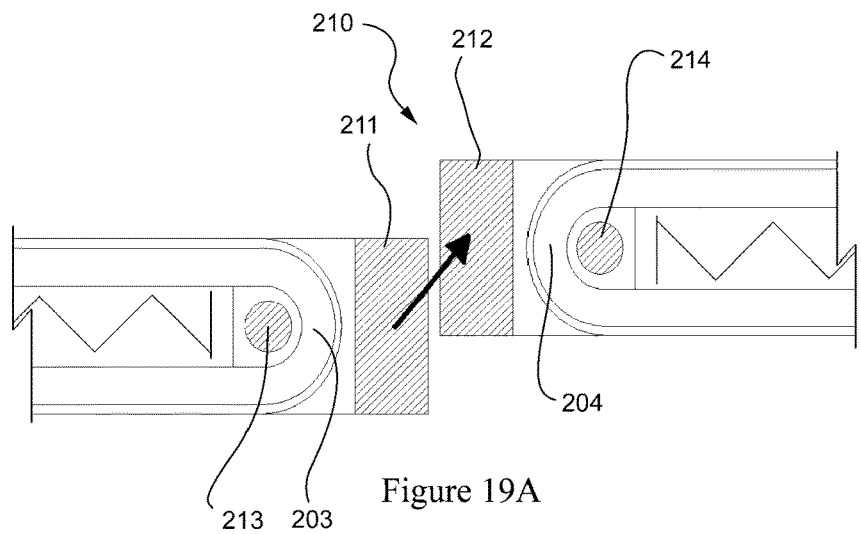
FIGS. 19A-19F illustrate a variety of methods for joining the split aortic annuloplasty ring illustrated in FIG. 18A.
Figure 19B:
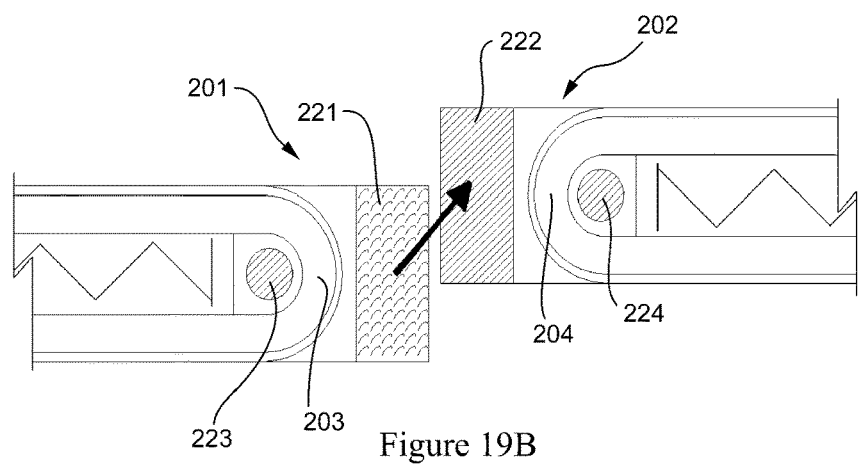
Figure 19C:
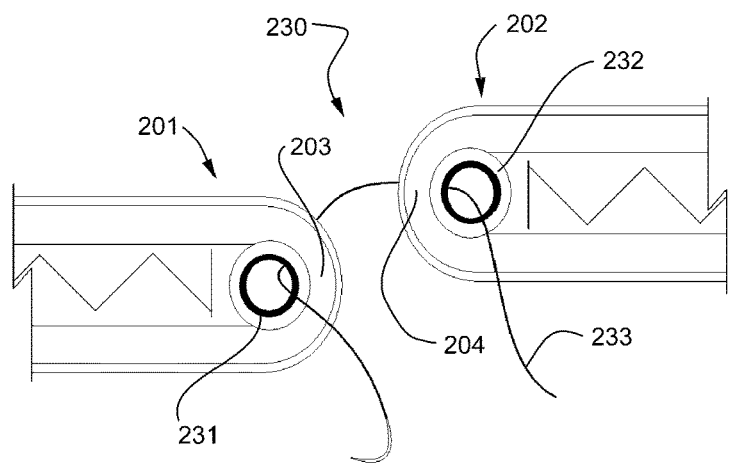
Figure 19D:
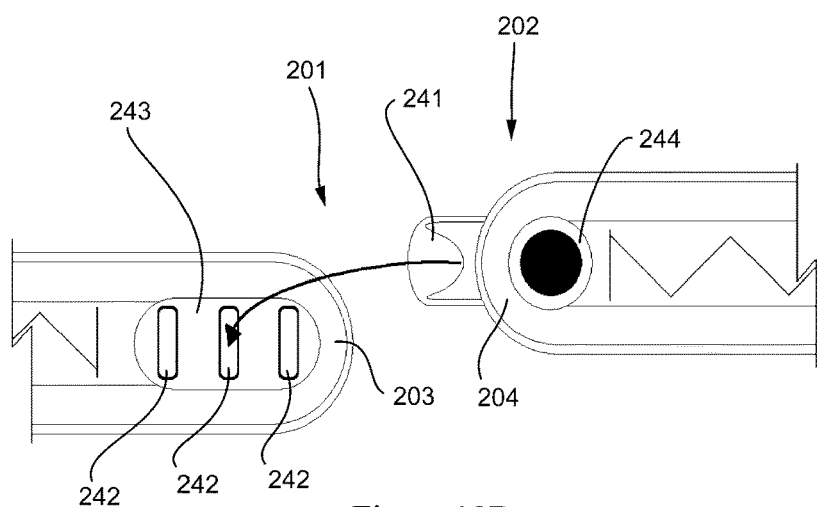
Figure 19E:
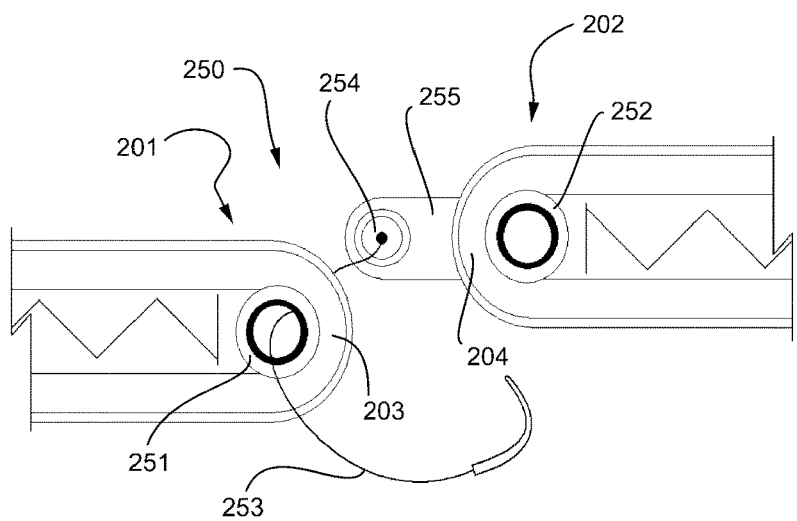
Figure 19F:
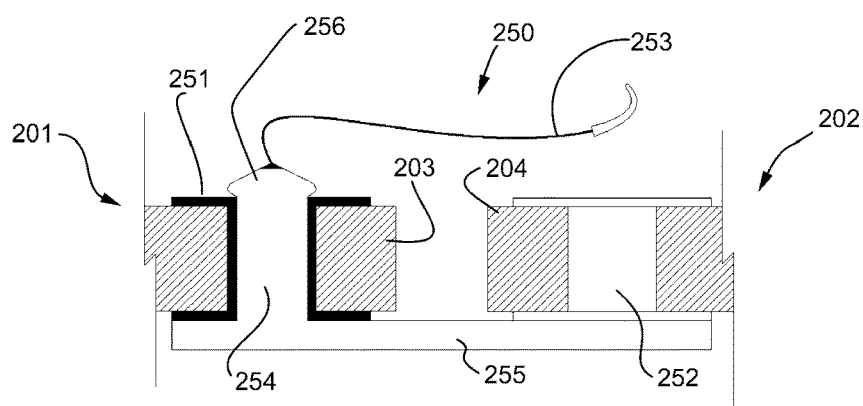
Figure 20A:
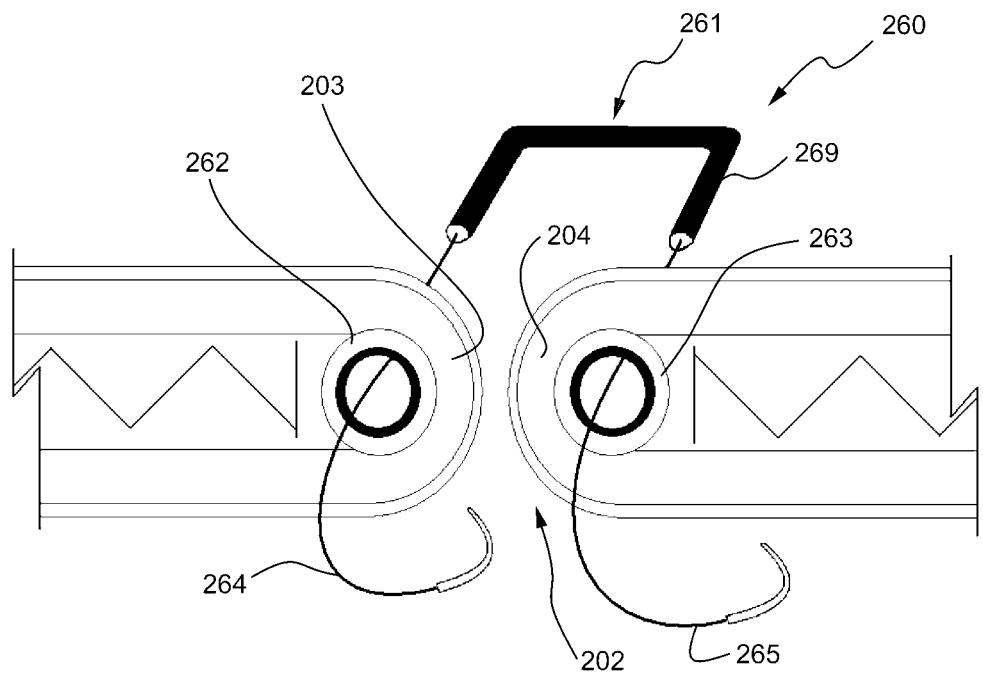
FIGS. 20A-20B illustrate a further variant for joining the ends of split annuloplasty ring of FIG. 18A.
Figure 20B:
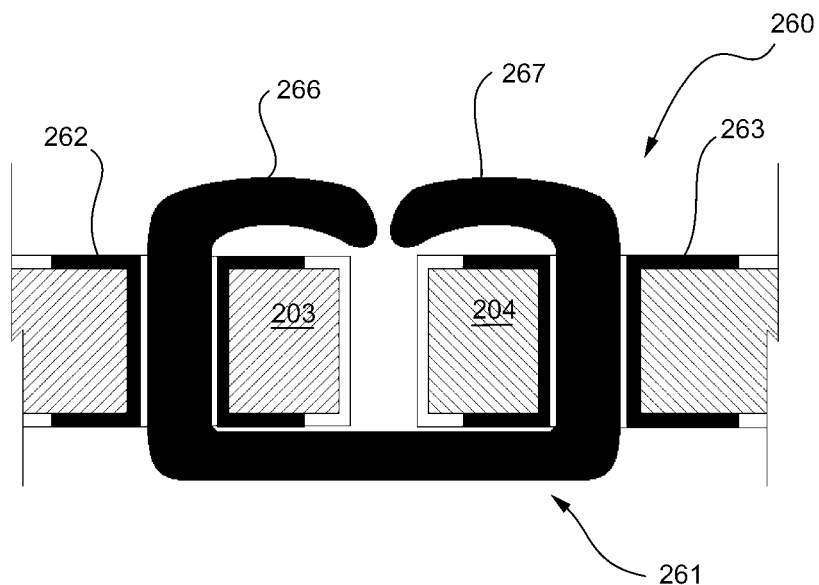

With reference to FIGS. 18 to 20, the features of strip, band or split ring 10' will now be described in greater detail below.

Figure 18A:
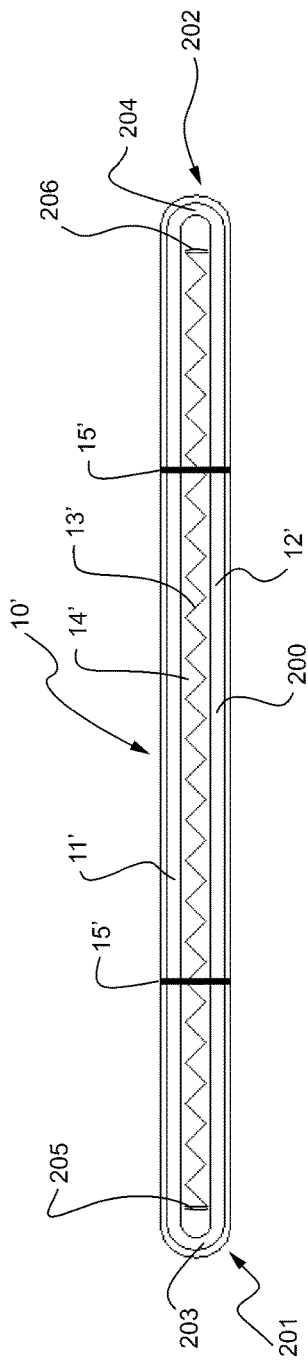
FIGS. 18A-18B illustrate a split aortic annuloplasty ring according to the present invention.
Figure 18B:
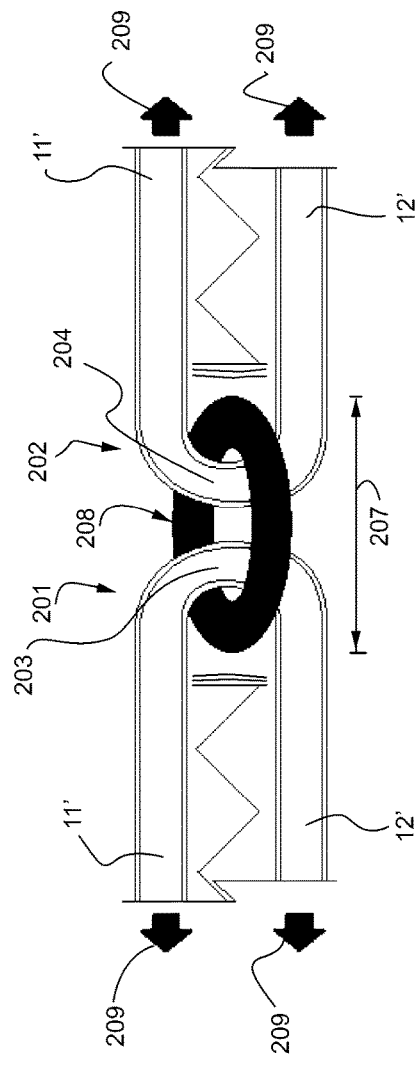

As illustrated in FIG. 18A, split ring 10' consists of a unitary elastomeric core 200 having a perimeter length approximately twice the circumference of the eventual closed ring resulting when first 201 and second ends 202 of ring are joined.

Elastomeric core 200 consists of four segments 11', 12', 203, 204. The cross-section of said segments of elastomeric core 200 is similar to the cross section of core members 11 or 12 in complete ring 10 described in FIG. 1. Stitch 13' is similar to stitch 13 of complete ring 10. A method of fabrication split ring 10' includes inserting the elastomeric core 200 in an elongate textile sheath 16' provided with a suitable insertion opening that is sutured closed once core 200 is inserted therein. Stitch 13' may then be sewn in between top 11' and bottom 12' segments of elastomeric core 200 along the length of split ring 11'. Stitch 13' terminates at a first 205 and second 206 tack, said tacks aiding to keep first 201 and second 202 end segments of elastomeric core 200 located relative to textile sheath 16' and from loading stitch 13'. An array of markers 15' may be provided in textile sheath 16' in a spaced apart orientation to assist the surgeon in correctly placing the ring-retention sutures that will serve to fix split ring 10' to the native aortic root NAR.

Various embodiments are possible for joining free ends 201, 202 of split ring 10'. FIG. 19A illustrates a glued mechanical joint 210. Split ring 10' is configured with two cooperating flaps 211, 212 of fabric extending longitudinally beyond terminal ends 201,202 of split ring 10'. Said flaps are preferably made from same fabric as textile sheath 16'. Each of flaps 211, 212 is connected or attached to its respective reinforcement member 213, 214. When said flaps are joined, reinforcements 213, 214 ensure that the hoop stresses exerted on the joined ring from the resized and pulsating aortic root are effectively transferred from the glued joint at joined flaps 211,212 to the reinforcements 213, 214 and consequently to end segments 203,204 of elastomeric core 200. Any quick curing bioglue suitable for implantation in the human body, and for gluing textiles such as Dacron or ePTFE may be used.

FIG. 19B illustrates a Velcro® type mechanical joint 220. Split ring 10' is configured with two cooperating members, a Velcro® hook member 221 and a Velcro® loop member 222, each extending longitudinally beyond terminal ends 201,202 of split ring 10'. Each of members 221,222 is connected or attached to its respective reinforcement member 223, 224 for same reasons as mechanical joint 210 of FIG. 19A. A Velcro® mechanical joint 220 advantageously allows surgeon to detach and reattach ring free ends 201, 202 during the surgical process. One of the cooperating members 222 or 221 may also be advantageously configured with longer length than its cooperating member 221 or 222 so as to provide a degree of adjustability in setting the overall circumference of the joined split ring 10'. This feature provides some degree of adjustability in allowing the surgeon to fine tune the leaflet coaptation in diastole.

FIG. 19C illustrates a mechanical joint 230 that is joined by a filament member or thread 233. Ends 201, 202 of ring 10' are configured with eyelets 231, 232 to evenly distribute the closing load provided by thread 233 over the elastomeric end segment 203, 204 respectively.

FIG. 19D illustrates a mechanical joint 240 including a cooperating hook member 241 and slot member 242. Hook member 241 is coupled to end 202 through an eyelet or reinforcement member 244 serving to evenly distribute the ring-closing load over the elastomeric end segment 204. Hook member 241 extends away from end 202 and is configured to engage one of the plurality of slots 242 in end 201 of split ring 10'. Slots 242 are configured in reinforcement or insert or plate 243 serving to evenly distribute the ring-closing load over the elastomeric end segment 203. The plurality of slots 242 provides a degree of adjustability in setting the overall circumference of the joined split ring 10'

FIGS. 19E-19F illustrate a mechanical joint 250 including a cooperating plug member 254 and eyelet or catch member 251. Insertable plug member 254 is configured on a plate 255 which extends from end 202. Plug member 254 is coupled to end 202 through an assembled and permanently attached plug 252 serving to evenly distribute the ring-closing load over the elastomeric end segment 204. Plug 254 may be provided with a filament or thread member 253 extending therefrom to help surgeon guide said plug into engagement into cooperating eyelet 251. Plug 254 is configured with a deformable conical enlargement 256 to help guide it through eyelet 251 and once inserted to prevent it from being released from eyelet 251. As such, a secure and safe mechanical joint is achieved. Eyelet 251 is sized to evenly distribute the ring-closing load over the elastomeric end segment 203.

FIG. 20A illustrates a mechanical joint 260 including a separate coupling member 261 cooperating with eyelets 262, 263 in each of free ends 201, 202. Coupler 261 is preferably preformed in a U-shaped configuration having a spacing between members 268, 269 suitable to engage eyelets 262, 263. Coupler 261 is preferably provided with filament members or flexible guides or sutures 264, 265 extending from free ends of members 268, 269 to help surgeon guide coupler into engagement with respective eyelets 262, 263. Once engaged with said eyelets, coupler 261 is deformed to create bent over tabs 266, 267 that prevent disassembly of joint. Tabs 266, 267 may be deformed by a surgical tool, forceps, or may be preferably self-deforming by virtue of their shape memory alloy properties. Another example of a preferred embodiment for coupler 261 in nature of self-closing clip is described and illustrated in FIG. 9 of U.S. Pat. No. 6,921,407 to Nguyen.

In use, when the free ends 201, 202 of split ring 10' are coupled or joined by any one of the various embodiments described above, the loads exerted by the resized and pulsating aortic root to the annuloplasty ring will be essentially transferred to the elastomer core 200. Core segments 11', 12' are in tension 209 by virtue of the effective load transfer occurring at the mechanical joints 208 (schematically represented in FIG. 18B) described hereabove. Other alternative embodiments for split ring joints are also possible that effectively transfer the aortic root loads to the elastomeric core 200 when free ends 201, 202 of split ring 10' are suitably joined, thereby ensuring that the textile sheath 16' and stitch 13' are not load bearing members. As such, joined split ring 10' behaves similarly to complete ring 10 with textile sheath 16' allowing substantially unhindered expansion of elastomeric core 200 therewithin when it is exposed to cardiac cycle variations. It is appreciated that the portion of the ring over joint length 207 (schematically illustrated in FIG. 18B) may not be as elastic as the remainder of the ring outside this zone, as this depends on the mechanical properties of the different mechanical joint concepts.

With reference to FIGS. 14A-14D and 16A-16E, in surgeries requiring the resection of aneurysmal aortic tissue, an example of the implantation procedure for the proposed annuloplasty ring 10, includes the following steps:
measure the diameter of the ascending aorta (AA), diameter of the base of the aortic annulus, and wall thickness of the aortic root;
resect away the area surrounding the AA, leaving the aorta free from the pulmonary artery;
trim back the AA to about 5 mm above the commissure peaks;
scallop the aortic root tissue, removing aneurysmal Sinus of Valsalva tissue and leaving a fringe of aortic root tissue extending approximately 3 to 5 mm above the leaflet junction or leaflet insertion line;
separate the left ventricular outflow tract (LVOT) away from the base of the aortic root as far down as possible until muscular tissue is exposed;
resect the coronary ostia from the resected Sinus of Valsalva tissue and preserve for later reimplantation;
at the top of each commissure, pass three mobilization sutures to help mobilize resected aortic root and aortic valve mechanism;
in a subvalvular plane approximately 1 mm below the leaflet insertion line, pass five ring securing sutures. Three of the sutures 901, 903, 905 are aligned with each of the leaflet nadirs, one of the sutures 902 is placed at the base of the interleaflet triangle ILT between the left and right leaflet cusps, and one of the sutures 904 is placed between the left and non-coronary leaflet cusps.
preferably, ring securing sutures 901, 902, 903, 904, 905 are inserted from the inside of the subvalvular apparatus as U-stitches, and emerge from the ventricular tissue approximately 5 mm away from the outer aortic wall tissue. This distance is desirable in order to leave enough clearance for seating the ring, thus ensuring its position as low as possible on the left ventricular outflow tract. A ring securing suture is preferably not placed in the interleaflet triangle ILT between the right and non-coronary leaflet cusps in order to avoid potential interference with the AV node of bundle of HIS.
place three graft-securing sutures 909, 910, 911 aligned with the nadirs, above the leaflet insertion line 912, and pass through the scalloped aortic root fringe 913. These sutures are placed as U-stitches, going from the inside to the outside of the aortic root, as seen in FIG. 16A.
make three equally spaced cuts along the three vertical axial side marks of a vascular prosthesis VC such as a Gelweave Valsalva (Vascutek Terumo Inc.), extending up to the junction line joining the vertical and horizontal pleats of the vascular conduit (in aortic valves with approximately equally spaced commissures and leaflet sizes);
scallop the vascular conduit to recreate three pseudo-sinuses of Valsalva 914;
suture the scalloped vascular conduit to the native scalloped aortic root 915. Sutures are preferably placed along the aortic root tissue fringe, running from the nadir to the commissure (i.e. repeated 6 times), thereby always maintaining the sewing direction from the inside of the aortic root to the outside in order to avoid the risk of leaflet puncture, to ensure accurate and consistent suture placement with respect to leaflets, and to reduce the likelihood of bunching up vascular conduit at commissure location;
tie knots between adjacent sutures at the commissure location;
once the vascular conduit has been completely sutured to the scalloped portion of the native aortic root, the five ring securing sutures (i.e. U-stitches) are passed through the annuloplasty ring 10 from the inner to the outer surface, through each of suture windows 101;
descend the annuloplasty ring 10 through manipulation of holder assembly 100 in a manner to set ring 10 firmly in place at the base of the aortic valve annulus, or slightly therebelow;
holder assembly 100 is oriented such that the mechanical joint 106 is aligned with the AV node. Since there is no U-stitch suture in this location, this ensures that no ring securing sutures are placed in this region;
tie knots at the location where each of the five ring-securing sutures extend through the ring 10;
reimplant coronary button CB containing the native coronary ostia to the vascular conduit in the location of the new pseudo-sinuses.

Figure 15A:
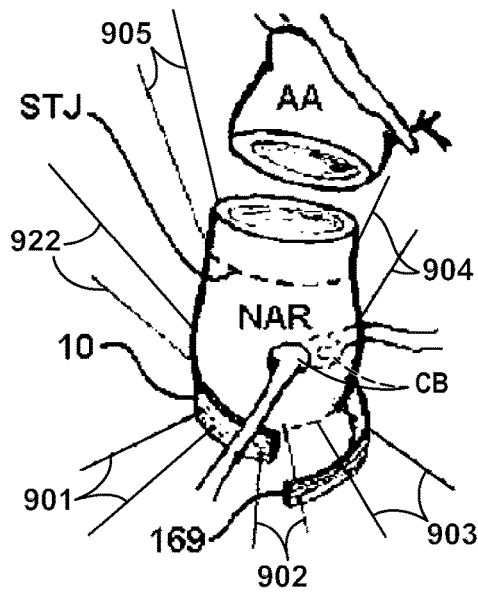
FIGS. 15A-15D in schematic elevational views illustrate the implantation steps of a pair of aortic annuloplasty rings of FIG. 1 in a leaflet valve sparing surgery whereby the native aortic root has been preserved.
Figure 15B:
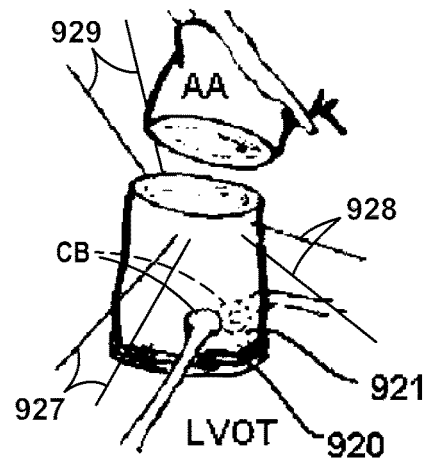
Figure 15C:
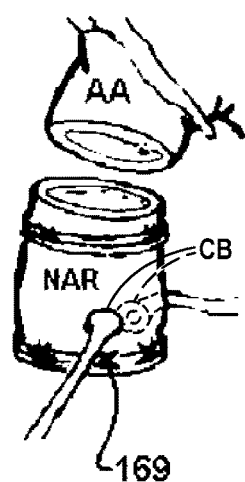
Figure 15D:
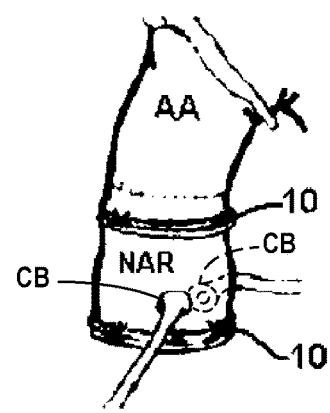

With reference to FIGS. 15A-15D and 17A-17C, in surgeries not requiring the resection of aneurysmal aortic tissue, an example of the implantation procedure for the proposed annuloplasty ring 10, includes the following steps:
cut the ascending aorta (AA), approximately 10 mm above the sinotubular junction (STJ);
measure the diameter of the ascending aorta, diameter of the base of the aortic annulus, diameter of the sinotubular junction and wall thickness of the aortic root;

resect away the area surrounding the AA, leaving the aorta free from the pulmonary artery;

separate the left ventricular outflow tract (LVOT) away from the base of the aortic root as far down as possible until muscular tissue is exposed;

create a space 920 between the right coronary artery and the base of the aortic root, directly below its point of departure from the right coronary sinus, such that the open ring can be fed through the space;

repeat the previous step for the left coronary artery, creating a space 921 between the left coronary artery and the base of the aortic root;

in a subvalvular plane approximately 1 mm below the leaflet insertion line, pass five ring securing sutures. Three of the sutures 901, 903, 905 are aligned with each of the leaflet nadirs, one of the sutures 902 is placed at the base of the interleaflet triangle ILT between the left and right leaflet cusps, and one of the sutures 904 is placed between the left and non-coronary leaflet cusps.

preferably, ring securing sutures 901, 902, 903, 904, 905, 906, 907 are inserted from the inside of the subvalvular apparatus as U-stitches, and emerge from the ventricular tissue approximately 5 mm away from the outer aortic wall tissue. This distance is desirable in order to leave enough clearance for seating the ring, thus ensuring its position as low as possible on the left ventricular outflow tract. A ring securing suture is preferably not placed in the interleaflet triangle ILT between the right and non-coronary leaflet cusps in order to avoid potential interference with the AV node of bundle of HIS, but can be placed if desired 922.

preferably, two of the five ring securing sutures 904 and 905 corresponding to the non-coronary leaflet nadir and the interleaflet triangle ILT between the left and non-coronary leaflet cusps, are passed through the space between the left coronary and the base of the aortic root;

pass the ring securing sutures (i.e. U-stitches) through the appropriate locations on the inner aspect of the open ring 923;

preferably, ring closing sutures 924 are placed through the right coronary end of the open ring prior to ring placement around the aortic annulus in order to avoid having to perform this step in situ;

pass the appropriate end of the ring 926 through the space between the left coronary and the base of the aortic root 921, ensuring that tension is maintained in the ring securing sutures to avoid tangling during placement;

pass the ring closing sutures and remaining end of the ring 925 through the space between the right coronary and the base of the aortic root 920, ensuring that tension is maintained in the ring securing sutures to avoid tangling during placement;

pass the ring closing sutures through the opposite end of the ring 926, pull the two ends of the ring together, tie knots, and trim the suture leads such that the ends of the ring are touching each other but not crimped or overlapping, forming a mechanical joint 169 between the two ends;

at this time the mechanical joint 169 of the two ends 925, 926 of the open ring should preferably lie approximately below the interleaflet triangle ILT between the non-coronary and right coronary leaflet cusps;

FIG. 15A shows another possible implantation orientation, where the mechanical joint 169 of the two ends lies approximately below the nadir of the right coronary leaflet cusp;

for each ring securing suture, remove slack by pulling the suture tight, knot the two ends, and trim the suture leads;

at this point the annulus ring placement is complete, and the STJ ring placement begins;

preferably, six ring securing sutures are placed in a plane approximately 5 mm above the STJ, three directly above the leaflet commissures 927, 928, 929, and three more equidistant between the first three, such that when the ring is placed, there is about 2 mm between the bottom of the ring and the leaflet commissures, and about 2 mm between the top of the ring and the cut edge of the ascending aorta to leave sufficient exposed tissue for anastomosis of the ascending aorta;

six ring securing sutures (i.e. U-stitches) are passed through the STJ annuloplasty ring 10 from the inner to the outer surface, through each of the suture windows 101;

descend the annuloplasty ring 10 through manipulation of holder 100 in a manner to place the ring in a plane slightly above the STJ;

for each of the six ring securing sutures, remove slack, tie knots, and trim suture leads;

test valve competency by filling the valve leaflets with saline solution and evaluating the characteristics of closure of the valve;

cut the ring holder retaining sutures, and remove the ring holder from the implantation site;

close the aortotomy by performing an anastomosis of the ascending aorta.

Figure 21:
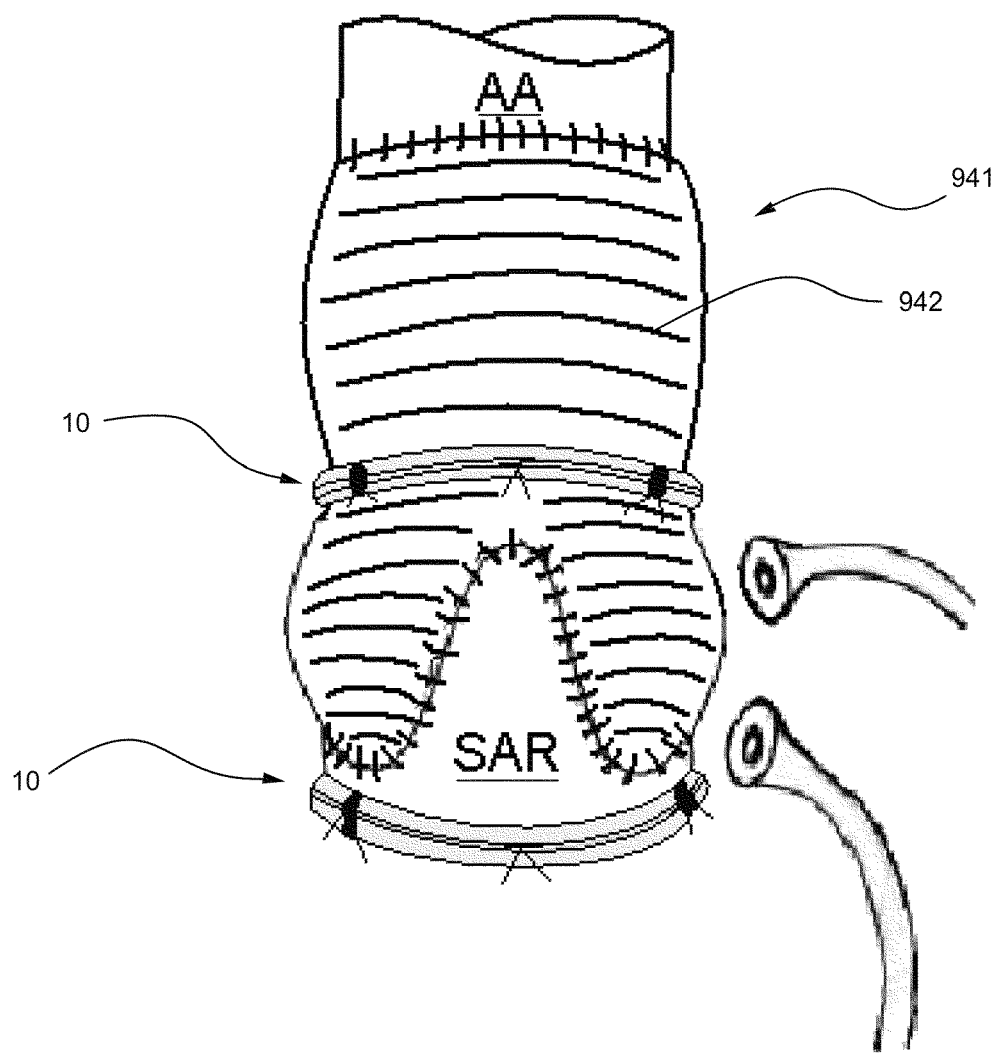
FIG. 21 illustrates a different embodiment for a double annuloplasty ring surgery used with oversized vascular conduits to replace aneurysmal aortic tissue.

With reference to FIG. 21, a different embodiment for a double annuloplasty ring concept is described. Unlike embodiment of FIGS. 15A-15D which uses double annuloplasty in cases where aortic tissue is not resected (i.e. aortic insufficiency without aneurysm of the aorta) this embodiment is suitable in cases where oversized conduits 941 are used to replace aneurysmal tissue and the resizing of both the base of aortic root and sinotubular junction are achieved by separate cooperating annuloplasty rings 10. Such conduits 941 may be prepared prior to surgery with annuloplasty ring 10 already coupled to graft at level of STJ.

An externally placed annuloplasty ring 10, 10' according to the present invention provides the following advantages:

since ring 10;10' is placed on the outside of the aortic root, ring core members 11,12;11',12' act as hoop members or brace members to inwardly constrain body tissue. As such, core members 11,12; 11',12' carry substantially the entire mechanical load associated with resizing a dilated aortic root (or aortic valve annulus), and relatively few U-stitch sutures are required to secure ring 10 to aortic root since said sutures only serve to locate ring axially relative to aortic root.

No contact with patient's blood flow eliminates the likelihood of thromoembolisms (or other such complications associated with prosthetics in contact with blood flow) and reduces the likelihood of post-implant infections.

Maximum flow-through area across the aortic valve, and minimum impact of valve leaflet dynamics.

Internally placed aortic annuloplasty rings as described in the prior art are associated with numerous drawbacks, including the technical challenge of intravascular implantation in a manner to not interfere with leaflet motion. As well, ring fixation sutures are critically stressed in internally placed aortic rings since the aortic annulus pulls away from the ring annulus during the systolic phase of the cardiac cycle. With internally placed annuloplasty rings the ring hoop structure retains the native aortic root through the fixation sutures and does not provide a buttressing effect as does an externally placed annuloplasty ring according to the principles of the present invention.

Figure 22A:
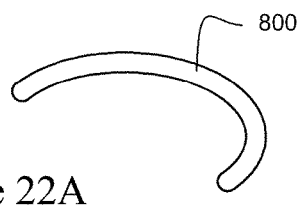
FIGS. 22A-22D illustrate the benefits a holder assembly illustrated in FIG. 5 advantageously applied to cardiac valve prosthesis in the nature of a mitral annuloplasty ring holders.
Figure 22B:
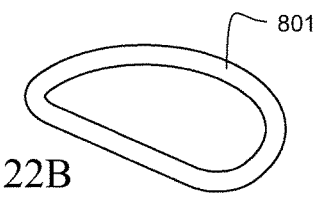

FIGS. 22A through 22D and 23A through 23D refer to further aspect of the present invention. The benefits of a holder system or assembly 100 for aortic annuloplasty ring 10 as described hereinabove may be advantageously applied to other types of annuloplasty rings. FIG. 22A shows an exemplary embodiment of a C-shaped mitral ring 800. FIG. 22B shows an exemplary embodiment of a D-shaped mitral ring 801. Mitral rings 800, 801 are releasably connected to a prosthesis carrier or holder body 850 through a ring retaining means such as a retaining suture (not shown). Holder body 850 is configured with a spherical boss or ball member 803 (FIG. 22C) similar to ball member 453 described in FIGS. 8A-8H. Holder body 850 is demountably and pivotingly coupled to handle member 804 (FIG. 22D) through ball-and-socket type mechanical joint 806 according to the principles of the present invention as described in FIGS. 8A-8H. As such holder assembly 810 benefits from the same inventive advantages as holder assembly 100.

Figure 23A:
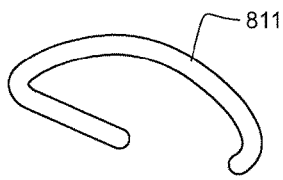
FIGS. 23A-23D illustrate the benefits a holder assembly illustrated in FIG. 5 advantageously applied to cardiac valve prosthesis in the nature of tricuspid annuloplasty ring holders.
Figure 23B:
Figure 22C:
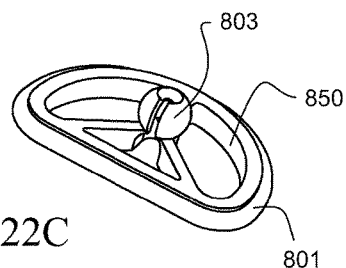
Figure 23C:
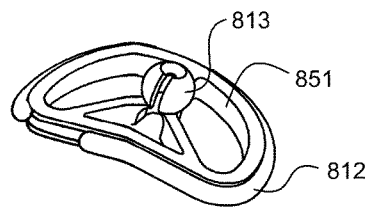
Figure 22D:
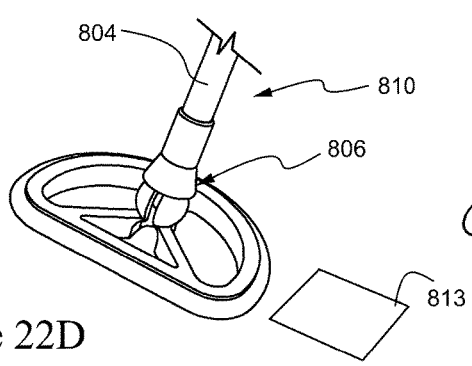
Figure 23D:
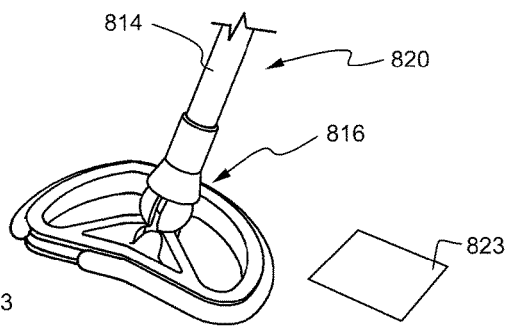

FIGS. 23A and 23B show exemplary embodiments of open tricuspid annuloplasty ring 801. Tricuspid rings 811, 812 are releasably connected to a prosthesis carrier or holder body 851 through a ring retaining means such as a retaining suture (not shown). Holder body 851 is configured with a spherical boss or ball member 813 (FIG. 23C) similar to ball member 453 described in FIGS. 8A-8H. Holder body 851 is demountably and pivotingly coupled to handle member 814 (FIG. 23D) through ball-and-socket type mechanical joint 816 according to the principles of the present invention as described in FIGS. 8A-8H. As such holder assembly 820 benefits from the same inventive advantages as holder assembly 100.

Unlike the aortic annuloplasty ring 10, rings 800, 801, 811, 812 are mounted within a heart chamber and as such ball member 803, 813 is preferably located inwardly from the annulus of rings 800, 801, 811, 812, and, in use, inwardly from the native valve annulus being repaired.

The holding assembly according to the principles of the invention may be applied to any of the commercially available annuloplasty rings whose implantation may be facilitated by a holder and a handle coupled thereto. These include stiff or flexible rings, split or continuous rings, and those available in a variety of shapes including C-shaped, D-shaped, kidney-shaped, saddle-shaped, or non-planar shaped.

Figure 24A:
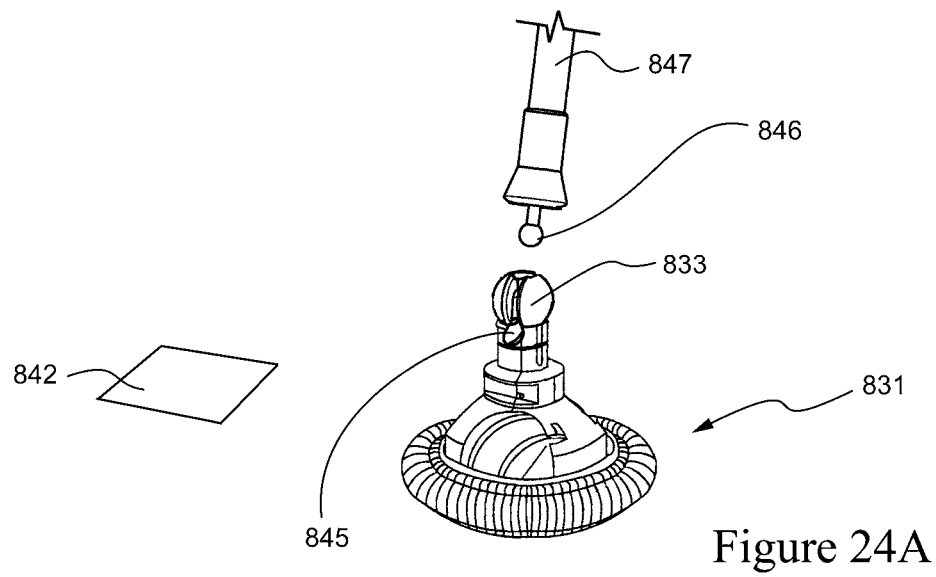
FIGS. 24A-24B illustrate the benefits a holder assembly illustrated in FIG. 5 advantageously applied to cardiac valve prosthesis in the nature of a mechanical heart valve.
Figure 24B:
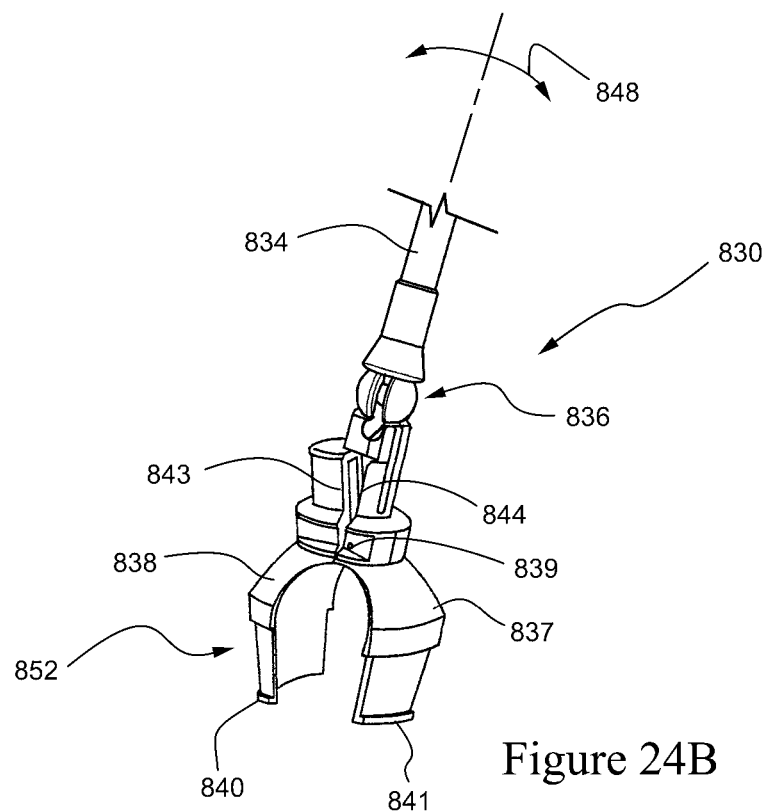

FIGS. 24A-24B refer to further aspect of the present invention. The benefits of a holder system or assembly 100 for aortic annuloplasty ring 10 as described hereinabove may be advantageously applied to other types cardiac valve prostheses such as a mechanical heart valve 831. Valve 831 defines a prosthesis plane 842. A typical holder body 852 suitable for releasably holding a mechanical valve is illustrated. Body 852 is provided with two cooperating half members 838, 837 which are pivotingly coupled through joint 839. Members 838, 837 are each provided with a tang 840, 841, respectively, to retain mechanical valve 831 when said members are in their valve retaining configuration (FIG. 24A) and to release said valve when said members are in their releasing configuration (FIG. 24B). Members 837, 838 are held in their retaining configuration typically by a filament or suture (not shown) which keeps faces 843, 844 in contact. To release said cardiac valve from holder body 852 after implantation the surgeon cuts said filament or suture thus allowing relative pivoting between members 837, 838.

A ball member 836 is configured atop one of said half members (837 as illustrated). Ball end 846 is insertable into passage 845 to pivotingly couple holder 852 to handle 847. During the surgical procedure the surgeon may adjust the orientation of the holder body relative to the handle or even release said holder from handle to exchange size of prosthesis, or even to changeover to a valve sizer implement instead of the holder body. To release the holder from the implanted valve 831, the handle may be advantageously manipulated while it is locked with holder body 852 along an angular motion 848 to facilitate the release of valve 831 from holder body 852.

The holder assembly 830 allows surgeon to select the most optimum orientation for handle 847 relative to valve 831 depending on the patient's specific anatomy, type of valve being implanted, type of surgical approach being employed (i.e. intercostal, sternotomy, or subxiphoid), or depending on surgeon work preference.

Figure 25:
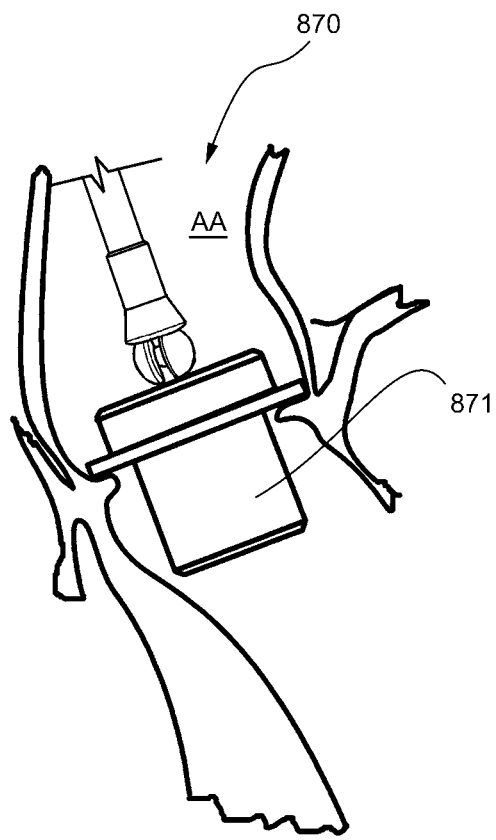
FIG. 25 illustrate the benefits a holder assembly illustrated in FIG. 5 advantageously applied to valve sizers for sizing an aortic valve during valve replacement surgery.
Figure 26:
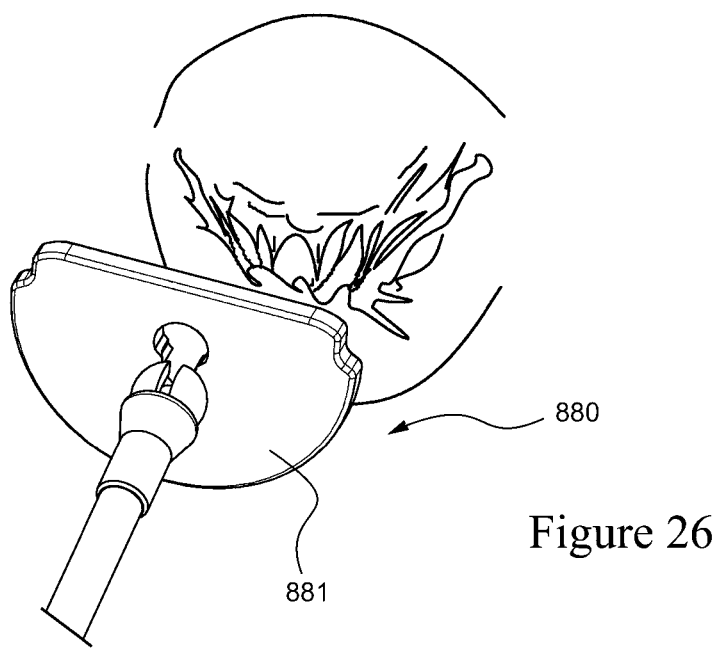
FIG. 26 illustrate the benefits a holder assembly illustrated in FIG. 5 advantageously applied to valve sizers for sizing a mitral valve during valve repair surgery.

FIGS. 25-26 refer to further aspect of the present invention. The benefits of a holder system or assembly 100 for aortic annuloplasty ring 10 as described hereinabove may be advantageously applied to other implements used in cardiac valve surgeries such as valve sizers used to determine the size of annuloplasty ring in valve repair surgeries (FIG. 26), or size of cardiac valve prosthesis in valve replacement surgeries (FIG. 25).

FIG. 25 illustrates a holding system or holder assembly 870 for releasably mounting aortic valve sizers 871 during an aortic valve surgery.

FIG. 26 illustrates a holding system or holder assembly 880 for releasably mounting mitral valve sizers or template 881 during a mitral valve repair surgery.

A holder assembly 870, 880 having a detachable holder and handle according to the present invention provides the surgeon with the ability for quick changeovers between different sizers, and eventually once size of prosthesis to be implanted is determined, a changeover from sizer to cardiac prosthesis, all changeovers being performed with a common handle member.

The coupling between the distal tip of the handle and the prosthesis holder or sizer template should be such that the two may be easily separated from the handle when desired, while at the same time should remain securely attached to the handle to prevent unintentional separation therefrom during surgery. The holding system according to the present invention provides many advantages over the prior art techniques allowing rapid changeovers between different sizing templates and/or prosthesis, offering variability in the range of orientation the prosthesis relative to handle may take, providing the ability to quickly and securely lock the cardiac prosthesis holder relative to handle in most suitable orientation for a given intervention.

The invention claimed is:

1. A prosthetic device for surgical repair of an aortic valve of a patient, the aortic valve being exposed to alternating diastolic and systolic phases of a cardiac cycle, the aortic valve having a valve axis and contained within a generally tubular aortic root, the aortic valve including a plurality of valve leaflets, the valve leaflets attached to a coronet-shaped valve annulus, the coronet-shaped valve annulus extending circumferentially around the valve axis, the coronet-shaped valve annulus extending in height along the valve axis between a nadir portion at a base of the aortic root and a spaced away commissure portion generally at a sinotubular junction of the aortic root, the aortic root also having a subvalvular region located below the nadir portion and a supravalvular region located above the commissure portion, the aortic root having coronary arteries attached thereto between the subvalvular and supravalvular regions, the prosthetic device comprising:
  a subvalvular ring, said subvalvular ring being annular in shape; and
  a supravalvular ring, said supravalvular ring being annular in shape;
  wherein, said subvalvular and supravalvular rings are configured, in use, as closed-perimeter flexible structures for placement externally around the aortic root, the subvalvular ring at the subvalvular region generally adjacent the nadir portion of the valve annulus, the supravalvular ring at the supravalvular region generally adjacent the commissure portion of the valve annulus, and whereby, in use, the closed-perimeter flexible structures cooperate to constrain the aortic root so as to improve coaptation of the valve leaflets during the diastolic phase of the cardiac cycle.

2. The prosthetic device of claim 1, wherein the subvalvular ring of the prosthetic device is configured with a ring height that is appropriate to allow surgical implantation of the subvalvular ring below the attachment point of the coronary arteries of the aortic root.

3. The prosthetic device of claim 2, wherein the subvalvular ring of the prosthetic device is configured as an elongate flexible open band having a first band end and second band end and a ring-closing member, said open band allowing the placement of the subvalvular ring below the attachment point of the coronary arteries without having to surgically detach the coronary arteries from the aortic root, the ring-closing member operative to couple said first and second band ends to form the closed-perimeter flexible structure of the subvalvular ring.

4. The prosthetic device of claim 2, wherein said subvalvular ring has elastic mechanical properties.

5. The prosthetic device of claim 2, wherein said supravalvular ring has elastic mechanical properties.

6. The prosthetic device of claim 3, wherein the supravalvular ring of the prosthetic device is configured as an elongate flexible member joined at respective core terminal ends to produce a single open band having a first band end and second band end and a ring-closing member, the ring-closing member operative to couple said first and second band ends to form the closed-perimeter flexible structure of the supravalvular ring.

7. The prosthetic device of claim 3, wherein the supravalvular ring has elastic mechanical properties.

8. The prosthetic device of claim 7, wherein the subvalvular ring has elastic mechanical properties.

9. The prosthetic ring of claim 8, wherein the supravalvular ring of the prosthetic device is configured as an elongate flexible member joined at respective core terminal ends to produce a single open band having a first band end and second band end and a ring-closing member, the ring-closing member operative to couple said first and second band ends to form the closed-perimeter flexible structure of the supravalvular ring.

10. The prosthetic device of claim 8, wherein said subvalvular and supravalvular rings are expandable as a function of the different phases of the cardiac cycle, said subvalvular and supravalvular rings being elastically expandable in annular perimeter between a first device configuration in which the aortic root is exposed to the diastolic phase of the cardiac cycle and a second device configuration of larger annular perimeter than said first device configuration in which the aortic root is exposed to a systolic phase of the cardiac cycle, in said first device configuration the prosthetic device having an appropriately sized first perimeter length so as to improve coaptation of the valve leaflets, and in said second device configuration the prosthetic device expands to a second perimeter length greater than said first perimeter length thereby allowing a controlled expansion of the aortic root as the valve leaflets open to allow blood flow through the open aortic valve.

11. The prosthetic device of claim 1, wherein at least one of said subvalvular or supravalvular rings is covered with a flexible fabric.

12. The prosthetic device of claim 11, wherein said fabric is a compliant textile material that allows substantially unhindered expansion of said subvalvular or supravalvular rings as said prosthetic device transitions between said first and second device configurations.

13. The prosthetic device of claim 12, wherein the supravalvular ring is comprised of first and second core members, said first and second core members being annular in shape, and said fabric maintains said first and second core members in a spaced-apart spatial relationship relative to one another in a manner to create an interspaced fabric portion between said core members for receiving a suture through said supravalvular ring during implantation of the prosthetic device to repair the aortic valve.

14. The prosthetic device of claim 13, wherein said fabric is provided with a plurality of circumferentially spaced apart position indicators serving as visual guides during the implantation of said supravalvular ring.

15. The prosthetic device of claim 13, wherein the subvalvular ring is comprised of a core member, said core member being elongate and having a longitudinal opening extending therethrough, and further including fabric extending across said longitudinal opening for receiving a suture through said subvalvular ring during implantation of the prosthetic device to repair the aortic valve.

16. The prosthetic device of claim 15, wherein said first and second core members of the supravalvular ring and said core member of the subvalvular ring are made from a silicone elastomer material, and said fabric is made from a knitted polyester fabric.

17. The prosthetic device of claim 15, wherein said fabric is provided with a plurality of circumferentially spaced apart position indicators serving as visual guides during the implantation of said subvalvular ring.

18. The prosthetic device of claim 10, wherein the prosthetic device expansion between said first and second device configurations is within an expansion range of 8% to 15%.

19. The prosthetic device of claim 10, wherein at least one of said subvalvular or supravalvular rings is configured with a cross-sectional area that varies as a function of the location along said annular perimeter thereof, so as to provide variable flexibility to said subvalvular or supravalvular rings depending on the circumferential location along said closed-perimeter structure thereof.

20. The prosthetic device of claim 10, wherein at least one of said subvalvular or supravalvular rings is reinforced by fibres or filament members thereby producing a fiber-reinforced arrangement, so as to provide a non-linear elasticity to said prosthetic device as it transitions between said first and second device configurations.

21. The prosthetic ring of claim 4, wherein said supravalvular ring has elastic mechanical properties.

22. A prosthetic device for surgical repair of an aortic valve of a patient, the aortic valve being exposed to alternating diastolic and systolic phases of a cardiac cycle, the aortic valve having a valve axis and contained within a generally tubular aortic root, the aortic valve including a plurality of valve leaflets, the valve leaflets attached to a coronet-shaped valve annulus, the coronet-shaped valve annulus extending circumferentially around the valve axis, the coronet-shaped valve annulus extending in height along the valve axis between a nadir portion at a base of the aortic root and a spaced away commissure portion generally at a sinotubular junction of the aortic root, the aortic root also having a subvalvular region located below the nadir portion and a supravalvular region located above the commissure portion, the aortic root having coronary arteries attached thereto between the subvalvular and supravalvular regions, the prosthetic device comprising:

a subvalvular ring; said subvalvular ring being annular in shape and covered by a flexible fabric, said subvalvular ring being further comprised of an elastic core member, said elastic core member having a longitudinal opening extending therethrough, said fabric extending across said longitudinal opening for receiving a suture through said subvalvular ring during implantation of the prosthetic device to repair the aortic valve; and a supravalvular ring, said supravalvular ring being annular in shape and covered by a flexible fabric;

wherein, said subvalvular and supravalvular rings are configured, in use, as closed-perimeter flexible structures for placement externally around the aortic root, the subvalvular ring at the subvalvular region generally adjacent the nadir portion of the valve annulus, the supravalvular ring at the supravalvular region generally adjacent the commissure portion of the valve annulus, and whereby, in use, the closed-perimeter flexible structures cooperate to constrain the aortic root so as to improve coaptation of the valve leaflets during the diastolic phase of the cardiac cycle.

23. The prosthetic device of claim 22, wherein the subvalvular ring of the prosthetic device is configured as an elongate flexible open band having a first band end and second band end and a ring-closing member, said open band allowing the placement of the subvalvular ring below the attachment point of the coronary arteries without having to surgically detach the coronary arteries from the aortic root, the ring-closing member operative to couple said first and second band ends to form the closed-perimeter flexible structure of the subvalvular ring.

24. The prosthetic device of claim 23, wherein the supravalvular ring is comprised of first and second elastic core members, said first and second elastic core members being annular in shape, said fabric of the supravalvular ring coupled to each of said first and second core members, said fabric of the supravalvular ring maintaining said first and second core members in a spaced-apart spatial relationship relative to one another in a manner to create an interspaced fabric portion between said elastic core members for receiving a suture through said supravalvular ring during implantation of the prosthetic device to repair the aortic valve.

25. The prosthetic device of claim 24, wherein said subvalvular and supravalvular rings are expandable as a function of the different phases of the cardiac cycle, said subvalvular and supravalvular rings being elastically expandable in annular perimeter between a first device configuration in which the aortic root is exposed to the diastolic phase of the cardiac cycle and a second device configuration of larger annular perimeter than said first device configuration in which the aortic root is exposed to a systolic phase of the cardiac cycle, in said first device configuration the prosthetic device having an appropriately sized first perimeter length so as to improve coaptation of the valve leaflets, and in said second device configuration the prosthetic device expands to a second perimeter length greater than said first perimeter length thereby allowing a controlled expansion of the aortic root as the valve leaflets open to allow blood flow through the open aortic valve.

* * * * *